United States Patent
Bamas-Jacques et al.

(10) Patent No.: US 7,604,970 B2
(45) Date of Patent: Oct. 20, 2009

(54) **VARIANTS OF THE PAPM POLYPEPTIDE OF BACTERIA OF THE *STREPTOMYCES* GENUS**

(75) Inventors: Nathalie Bamas-Jacques, Paris (FR); Denis Thibaut, Paris (FR); Alain Famechon, Janville Sur Juine (FR)

(73) Assignee: Aventis Pharma S.A., Paris (FR)

( * ) Notice: Subject to any disclaimer, the term of this patent is extended or adjusted under 35 U.S.C. 154(b) by 1532 days.

(21) Appl. No.: 10/603,282

(22) Filed: Jun. 25, 2003

(65) Prior Publication Data

US 2008/0188378 A1    Aug. 7, 2008

(30) Foreign Application Priority Data

Jun. 28, 2002    (FR)    ................................ 02 08057

(51) Int. Cl.
*C12N 9/10*        (2006.01)
*C12N 1/20*        (2006.01)
*C12N 15/00*       (2006.01)
*C07H 21/04*       (2006.01)

(52) U.S. Cl. ................. 435/193; 435/252.3; 435/320.1; 536/23.2

(58) Field of Classification Search ................ 435/193, 435/252.3, 320.1; 536/23.2
See application file for complete search history.

(56) References Cited

U.S. PATENT DOCUMENTS 6,352,839 B1    3/2002    Blanc

FOREIGN PATENT DOCUMENTS

WO    WO 96/05219    2/1996

OTHER PUBLICATIONS

Blanc, Veronique et al., Identification and analysis of genes from *Streptomyces pristinaespiralis* encoding enzymes involved in the biosynthesis of the 4-dimethylamino-l-phenylalanine precursor of pristinamycin I, Molecular Microbiology, (1997), vol. 23, No. 2, pp. 191-202.

*Primary Examiner*—Tekchand Saidha

(57) ABSTRACT

The present invention relates to novel variants of the PapM polypeptide of bacteria of the *Streptomyces* genus which possess a substrate selectivity and/or an improved effectiveness compared to the wild-type polypeptide. It also relates to the nucleic acids encoding these variants, to the microorganisms which incorporate these nucleic acids and to their use for producing B components of Streptogramins.

10 Claims, 13 Drawing Sheets

Figure 2:
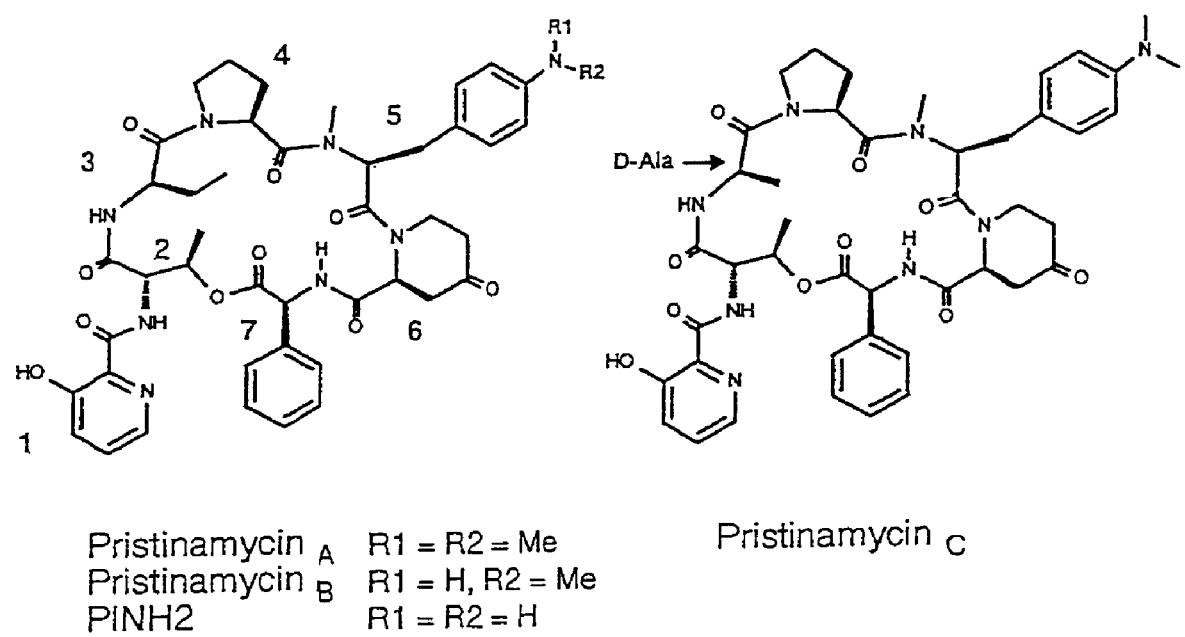

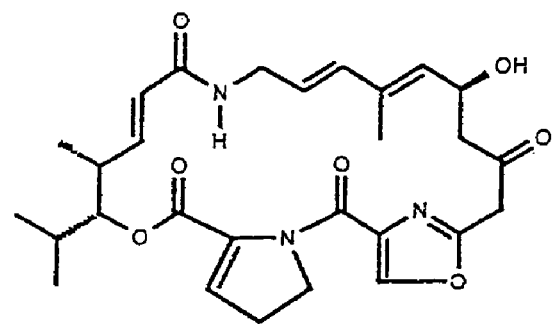 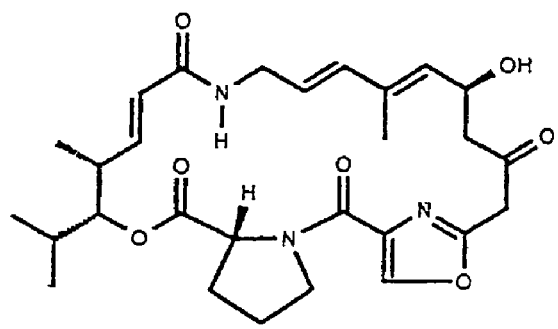
Pristinamycin II$_A$          Pristinamycin II$_B$
Figure 1

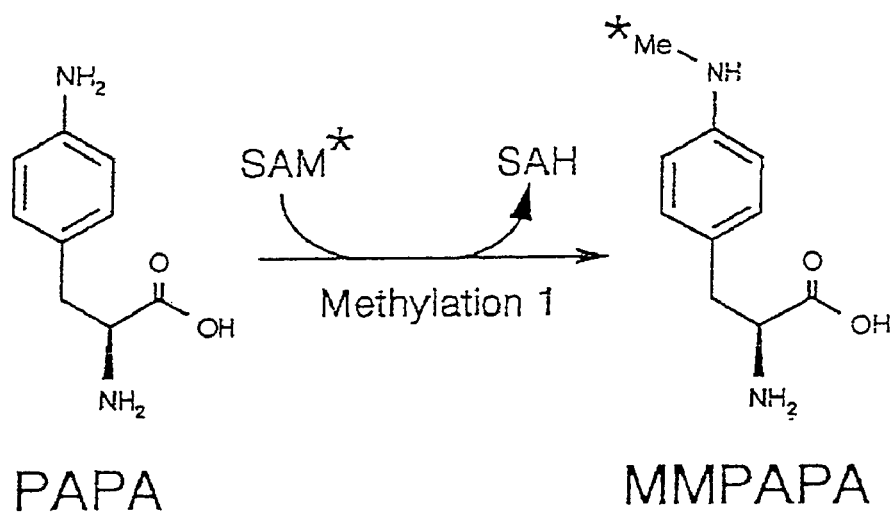
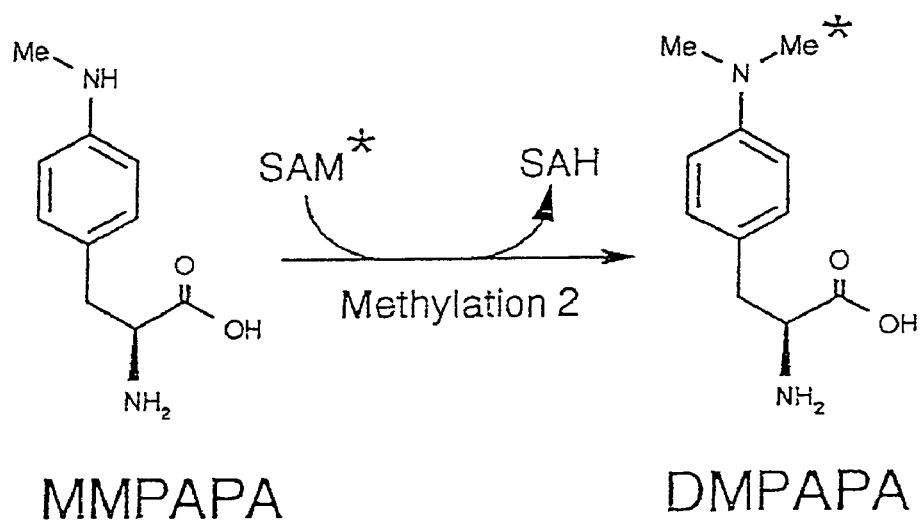
Figure 4

```
  M   T   A   A   A   P   T   L   A   Q   A   L   D   E   A   T   G   Q    18
GTG ACC GCC GCC GCA CCC ACC CTC GCC CAG GCG CTG GAC GAG GCC ACC GGG CAG    54

L   T   G   A   G   I   T   A   D   A   A   R   A   D   T   R   L   L    36
CTG ACC GGC GCC GGG ATC ACC GCC GAC GCC GCC CGG GCC GAC ACC CGG CTG CTG   108

A   A   H   A   C   Q   V   A   P   G   D   L   D   T   C   L   A   G    54
GCC GCC CAC GCC TGC CAG GTC GCC CCG GGG GAC CTC GAC ACC TGC CTG GCC GGC   162

P   V   P   P   R   F   W   H   Y   V   R   R   L   T   R   E   P        72
CCG GTG CCG CCC CGG TTC TGG CAC TAC GTC CGG CGC CGT CTG ACC CGC GAA CCC   216

A   E   R   I   V   G   H   A   Y   F   M   G   H   R   F   D   L   A    90
GCC GAA CGC ATC GTC GGC CAC GCC TAC TTC ATG GGC CAC CGC TTC GAC CTG GCC   270

P   G   V   F   V   P   K   P   E   T   E   E   I   T   R   D   A   I   108
CCC GGC GTC TTC GTC CCC AAA CCC GAG ACC GAG GAG ATC ACC CGG GAC GCC ATC   324

A   R   L   E   A   L   V   R   R   G   T   P   A   P   L   V   V   D   126
GCC CGC CTG GAG GCC CTC GTC CGC CGC GGC ACC CCC GCA CCC CTG GTC GTC GAC   378

L   C   A   G   P   G   T   M   A   V   T   L   A   R   H   V   P   A   144
CTG TGC GCC GGA CCG GGC ACC ATG GCC GTC ACC CTG GCC CGC CAC GTA CCG GCC   432

A   R   V   L   G   I   E   L   S   Q   A   A   A   R   A   A   R       162
GCC CGC GTC CTG GGC ATC GAA CTC TCC CAG GCC GCC GCC CGC GCC GCC CGG CGC   486

N   A   R   G   T   G   A   R   I   V   Q   G   D   A   R   D   A   F   180
AAC GCC CGC GGC ACC GGC GCC CGC ATC GTG CAG GGC GAC GCC CGC GAC GCC TTC   540
                                         Thr>Ile
  P   E   L   S   G   T   V   D   L   V   V   T   N   P   P   Y   I   P   198
CCC GAA CTG AGC GGC ACC GTC GAC CTC GTC GTC ACC AAC CCG CCC TAC ATC CCC   594
                                                  T     T   T       T
                    <<<<<<<<mutant66>>>>>>>>>>>>
  I   G   L   R   T   S   A   P   E   V   L   E   H   D   P   P   L   A   216
ATC GGA CTG CGC ACC TCC GCA CCC GAA GTG CTC GAG CAC GAC CCG CCG CTG GCC   648

L   W   A   G   E   E   G   L   G   M   I   R   A   M   E   R   T   A   234
CTG TGG GCC GGG GAG GAG GGC CTC GGC ATG ATC CGC GCC ATG GAA CGC ACC GCG   702
                                                         Gly>Ser
  A   R   L   L   A   P   G   G   V   L   L   L   E   H   G   S   Y   Q   252
GCC CGG CTG CTG GCC CCC GGC GGC GTC CTG CTC CTC GAA CAC GGC TCC TAC CAA   756
                                                       A
                                                   mutant49
  L   A   S   V   P   A   L   F   R   A   T   G   R   W   S   H   A   S   270
CTC GCC TCC GTG CCC GCC CTG TTC CGC GCA ACC GGC CGC TGG AGC CAC GCC TCG   810

S   R   P   T   C   N   D   G   C   L   T   A   V   R   N   H   T   C   288
TCC CGT CCC ACC TGC AAC GAC GGC TGC CTG ACC GCC GTA CGC AAC CAC ACC TGC   864

A   P   P   A   *                                                       293
GCA CCG CCC GCC TGA                                                       879
```

Figure 7

SEQUENCE LISTING

<160> NUMBER OF SEQ ID NOS: 2

<210> SEQ ID NO 1
<211> LENGTH: 1052
<212> TYPE: DNA
<213> ORGANISM: Streptomyces pristinaespiralis
<220> FEATURE:
<221> NAME/KEY: CDS
<222> LOCATION: (84)..(962)

<400> SEQUENCE: 1

```
ctcgaggacg agtggatcgc ctccggcggc gcccccgtcc ccacgcccgt gcacgcgtcc      60
gcgtccgcgc gggggccgt gtc gtg acc gcc gcc gca ccc acc ctc gcc cag     113
                     Val Thr Ala Ala Ala Pro Thr Leu Ala Gln
                      1               5                  10 gcg ctg gac gag gcc acc ggg cag ctg acc ggc gcc ggg atc acc gcc     161
Ala Leu Asp Glu Ala Thr Gly Gln Leu Thr Gly Ala Gly Ile Thr Ala
             15                  20                  25 gac gcc gcc cgg gcc gac acc cgg ctg ctg gcc gcc cac gcc tgc cag     209
Asp Ala Ala Arg Ala Asp Thr Arg Leu Leu Ala Ala His Ala Cys Gln
         30                  35                  40 gtc gcc ccg ggg gac ctc gac acc tgc ctg gcc ggc ccg gtg ccg ccc     257
Val Ala Pro Gly Asp Leu Asp Thr Cys Leu Ala Gly Pro Val Pro Pro
     45                  50                  55 cgg ttc tgg cac tac gtc cgg cgc cgt ctg acc cgc gaa ccc gcc gaa     305
Arg Phe Trp His Tyr Val Arg Arg Arg Leu Thr Arg Glu Pro Ala Glu
 60                  65                  70 cgc atc gtc ggc cac gcc tac ttc atg ggc cac cgc ttc gac ctg gcc     353
Arg Ile Val Gly His Ala Tyr Phe Met Gly His Arg Phe Asp Leu Ala
 75                  80                  85                  90 ccc ggc gtc ttc gtc ccc aaa ccc gag acc gag gag atc acc cgg gac     401
Pro Gly Val Phe Val Pro Lys Pro Glu Thr Glu Glu Ile Thr Arg Asp
                 95                 100                 105 gcc atc gcc cgc ctg gag gcc ctc gtc cgc cgg acc acc gca ccc         449
Ala Ile Ala Arg Leu Glu Ala Leu Val Arg Arg Gly Thr Thr Ala Pro
            110                 115                 120 ctg gtc gtc gac ctg tgc gcc gga ccg ggc acc atg gcc gtc acc ctg     497
Leu Val Val Asp Leu Cys Ala Gly Pro Gly Thr Met Ala Val Thr Leu
        125                 130                 135 gcc cgc cac gta ccg gcc gcc cgc gtc ctg ggc atc gaa ctc tcc cag     545
Ala Arg His Val Pro Ala Ala Arg Val Leu Gly Ile Glu Leu Ser Gln
    140                 145                 150 gcc gcc gcc cgc gcc gcc cgg cgc aac gcc cgc ggc acc ggc gcc cgc     593
Ala Ala Ala Arg Ala Ala Arg Arg Asn Ala Arg Gly Thr Gly Ala Arg
155                 160                 165                 170
```

```
atc gtg cag ggc gac gcc cgc gac gcc ttc ccc gaa ctg agc ggc acc      641
Ile Val Gln Gly Asp Ala Arg Asp Ala Phe Pro Glu Leu Ser Gly Thr
            175                 180                 185 gtc gac ctc gtc gtc acc aac ccg ccc tac atc ccc atc gga ctg cgc      689
Val Asp Leu Val Val Thr Asn Pro Pro Tyr Ile Pro Ile Gly Leu Arg
        190                 195                 200 acc tcc gca ccc gaa gtg ctc gag cac gac ccg ccg ctg gcc ctg tgg      737
Thr Ser Ala Pro Glu Val Leu Glu His Asp Pro Pro Leu Ala Leu Trp
    205                 210                 215 gcc ggg gag gag ggc ctc ggc atg atc cgc gcc atg gaa cgc acc gcg      785
Ala Gly Glu Glu Gly Leu Gly Met Ile Arg Ala Met Glu Arg Thr Ala
220                 225                 230 gcc cgg ctg ctg gcc ccc ggc ggc gtc ctg ctc ctc gaa cac ggc tcc      833
Ala Arg Leu Leu Ala Pro Gly Gly Val Leu Leu Leu Glu His Gly Ser
235                 240                 245                 250 tac caa ctc gcc tcc gtg ccc gcc ctg ttc cgc gca acc ggc cgc tgg      881
Tyr Gln Leu Ala Ser Val Pro Ala Leu Phe Arg Ala Thr Gly Arg Trp
                255                 260                 265 agc cac gcc tcg tcc cgt ccc acc tgc aac gac ggc tgc ctg acc gcc      929
Ser His Ala Ser Ser Arg Pro Thr Cys Asn Asp Gly Cys Leu Thr Ala
            270                 275                 280 gta cgc aac cac acc tgc gca ccg ccc gcc tga cacggcgtca cggcacggcc    982
Val Arg Asn His Thr Cys Ala Pro Pro Ala
                285                 290 ggcctgtcgg caacgaccct acgccattga caaaccgacc gtgccgtttt tttaatgtcg   1042
gggtggcgga                                                          1052

<210> SEQ ID NO 2
<211> LENGTH: 292
<212> TYPE: PRT
<213> ORGANISM: Streptomyces pristinaespiralis

<400> SEQUENCE: 2

Val Thr Ala Ala Ala Pro Thr Leu Ala Gln Ala Leu Asp Glu Ala Thr
 1               5                  10                  15

Gly Gln Leu Thr Gly Ala Gly Ile Thr Ala Asp Ala Ala Arg Ala Asp
            20                  25                  30

Thr Arg Leu Leu Ala Ala His Ala Cys Gln Val Ala Pro Gly Asp Leu
        35                  40                  45

Asp Thr Cys Leu Ala Gly Pro Val Pro Pro Arg Phe Trp His Tyr Val
    50                  55                  60

Arg Arg Arg Leu Thr Arg Glu Pro Ala Glu Arg Ile Val Gly His Ala
65                  70                  75                  80

Tyr Phe Met Gly His Arg Phe Asp Leu Ala Pro Gly Val Phe Val Pro
                85                  90                  95

Lys Pro Glu Thr Glu Glu Ile Thr Arg Asp Ala Ile Ala Arg Leu Glu
            100                 105                 110

Ala Leu Val Arg Arg Gly Thr Thr Ala Pro Leu Val Val Asp Leu Cys
        115                 120                 125

Ala Gly Pro Gly Thr Met Ala Val Thr Leu Ala Arg His Val Pro Ala
    130                 135                 140

Ala Arg Val Leu Gly Ile Glu Leu Ser Gln Ala Ala Arg Ala Ala
145                 150                 155                 160

Arg Arg Asn Ala Arg Gly Thr Gly Ala Arg Ile Val Gln Gly Asp Ala
                165                 170                 175

Arg Asp Ala Phe Pro Glu Leu Ser Gly Thr Val Asp Leu Val Val Thr
```

-continued

```
               180                 185                 190
Asn Pro Pro Tyr Ile Pro Ile Gly Leu Arg Thr Ser Ala Pro Glu Val
        195                 200                 205

Leu Glu His Asp Pro Pro Leu Ala Leu Trp Ala Gly Glu Glu Gly Leu
        210                 215                 220

Gly Met Ile Arg Ala Met Glu Arg Thr Ala Ala Arg Leu Leu Ala Pro
225                 230                 235                 240

Gly Gly Val Leu Leu Leu Glu His Gly Ser Tyr Gln Leu Ala Ser Val
                245                 250                 255

Pro Ala Leu Phe Arg Ala Thr Gly Arg Trp Ser His Ala Ser Ser Arg
                260                 265                 270

Pro Thr Cys Asn Asp Gly Cys Leu Thr Ala Val Arg Asn His Thr Cys
            275                 280                 285

Ala Pro Pro Ala
        290
```

VARIANTS OF THE PAPM POLYPEPTIDE OF BACTERIA OF THE *STREPTOMYCES* GENUS

The present invention relates to novel variants of the PapM polypeptide of bacteria of the *Streptomyces* genus which possess a substrate selectivity and/or an improved effectiveness compared to the wild-type polypeptide. It also relates to the nucleic acids encoding these variants, to the microorganisms which incorporate these nucleic acids and to their use for producing B components of Streptogramins.

Pristinamycin is an antibiotic which belongs to the streptogramin family to which virginiamycin and mikamycin also belong. Streptogramins form a small, homogeneous and original group of antibiotics consisting of a combination of two types of molecule which are chemically very different: streptogramins A are polyunsaturated macrolactones and streptogramins B are depsipeptides (Cocito C. G. (1979) *Microbiol. Rev.*, 43: 145-198) (Cocito C. G. (1983) *In Antibiotics* 6: (Ed. F. E. Hahn), 296-332). In the case of pristinamycin, the A and B compounds are called, respectively, pristinamycins II (PII) and pristinamycins I (PI), and their structures are represented in FIGS. 1 and 2.

The A and B compounds have a synergistic and bactericidal antibacterial activity particularly directed against Gram-positive bacteria such as Staphylococci and Enterococci (Cocito, 1979). These compounds act by attaching to the 50S subunit of the ribosomes of the target cells, which causes inhibition of protein synthesis (Cocito, 1979); (Di Giambattista M., Chinali G. and Cocito C. G. (1989) *J. Antim. Chemother.*, 24: 485-507).

Streptogramins are essentially produced by *Actinomycetes*. More particularly, pristinamycin is produced by the filamentous bacterium *Streptomyces pristinaespiralis* in the form of a natural mixture consisting of 30% of PI and 70% of PII (Blanc et al., (1995), J. Bacteriol. 177 (18): 5206-14). For each type of molecule, several isoforms are coproduced, as is commonly observed for natural metabolites.

In the case of pristinamycins PI (B components of pristinamycins), the major form produced is PIA, which consists of the following 7 residues linked to one another by amide bonds and an ester bond (FIG. 2): 3-hydroxypicolinic acid, L-threonine, D-aminobutyric acid, L-proline, 4-dimethylamino-L-phenylalanine, 4-oxo-L-pipecolic acid and L-phenylglycine. Several natural isoforms are also coproduced with the PIA and correspond to structural modifications relating mainly to the following residues: D-aminobutyric acid, 4-dimethylamino-L-phenylalanine (L-DMPAPA) and 4-oxo-L-pipecolic acid (Thibaut et al., (1997) J. Bacteriol. 170(3):697-704). These minor forms are synthesized with varying percentages depending on the strains of *S. pristinaespiralis*, which remain overall of the order of a few percent, the PIA representing from 90% to 95% of the PI produced. It is in particular noted that the various strains of *S. pristinaespiralis* synthesize approximately 5% of PIB, which differs from PIA by the presence of a 4-methylamino-L-phenylalanine (L-MMPAPA) in the 4-position of the macrocycle (FIG. 2). Although in the minority, PIB has been found to be a molecule which is particularly advantageous for its various pharmacological properties (WO 96/05219).

Another analog of PIA, PINH2, which differs by the presence of a 4-amino-L-phenylalanine in the 4-position (see FIG. 2) is of value for developing original products of hemisynthesis. To date, it has only been possible to obtain PINH2 in a method in which 4-amino-L-phenylalanine is added to the *S. pristinaespiralis* culture medium (WO 96/01901).

Several approaches have been envisioned for improving the production of streptogramins, a first approach is directed toward modifying the total proportion of A components (pristinamycins II) produced compared to the production of B components (pristinamycins I), another approach is directed toward modifying the proportion of the various isoforms present in each A or B components. However, no approach has, to date, made it possible to satisfactorily produce pristinamycin PIB, which remains a minor form of the B components (pristinamycins I) of pristinamycin.

A first approach, described in application WO 93/20182, consists of the selection of microorganisms capable of producing specifically the A components or the B components of the streptogramins. These microorganisms are obtained by conventional selection techniques comprising a first optional step of mutagenesis on a streptogramin-producing microorganism and a second step of identification of microorganisms selectively producing one or other of the A or B components of streptogramins. This technique makes it possible in particular to obtain strains of *S. pristinaespiralis* selectively producing pristinamycins PII (A component) or pristinamycins PI (B component). However, that document does not describe any strains which selectively produce pristinamycins PI with an isoform proportion modified in favor of the PIB form compared to PIA, which always remains the major form.

Application WO 94/08014 describes the isolation and identification of genes encoding enzymes involved in the biosynthetic pathway for the A components and in the biosynthetic pathway for the B components of streptogramins. It also describes the expression of these genes with the aim of increasing the levels of production of the A or B components, and the use of these genes for constructing mutants which are blocked at various steps of the biosynthetic pathways for the A or B components and which thus bring about the accumulation of certain intermediates of these biosynthetic pathways. More particularly, application WO 94/08014 describes the isolation and characterization of twelve genes, snaA, snaB, snaC, snaD, papA, papM, samS, snbA, snbC, snbD, snbE and snbR, isolated from a *S. pristinaespiralis* genomic DNA library and demonstrates the involvement of the snaA, snaB, snaC and snaD genes in the biosynthetic pathway for the A components and that of the papA, papM, samS, snbA, snbC, snbD, snbE and snbR genes in the biosynthetic pathway for the B components.

Thus, inactivation of the snaA gene in a strain of *S. pristinaespiralis* makes it possible to obtain a strain which no longer produces PIIA (one of the isoforms of the A components of pristinamycins) but produces only PIIB (the other isoform of the A components of pristinamycins) in an amount equivalent to the sum of PIIA and PIIB produced by the control strain carrying the wild-type form of the snaA gene. The production of PI (all the isoforms of the B components of pristinamycins) remains identical in the strains inactivated for the snaA gene and in the control strain.

Inactivation of the samS gene leads to the production of a strain which produces 35% less PIA (one of the isoforms of the B components of pristinamycins) and approximately 10 times more PIB (the other isoform of the B components of pristinamycins) compared to the control strain; the level of PIB then reaches 20% of all the total type I pristinamycins (PI) produced. Although the production of PIB is improved in these strains, the proportion of PIB is not major and remains less than that of PIA.

Inactivation of the papA gene or of the snbA gene leads to the production of strains which produce only pristinamycins of the PII type (A components) and which no longer produce pristinamycins of the PI type (B components).

Inactivation of the snaD gene makes it possible to obtain strains which, conversely, produce only pristinamycins of the PI type and which no longer produce pristinamycins of the PII type.

Application WO 96/01901 describes an original method for preparing novel compounds related to the B components of streptogramins but different from the B components naturally produced by streptogramin-producing microorganisms. According to this method, a strain of microorganism is used which is mutated so as to alter the biosynthesis of the precursors of the B components of streptogramins. As a mutant strain, use may in particular be made of strains of *S. pristinaespiralis* in which the biosynthetic pathway for the B component precursors is altered by disruption of the papA or pipA or hpaA genes. These strains no longer produce pristinamycins PI (B components) and produce pristinamycins PII (A components). The mutant strain is cultured in a medium supplemented with an original precursor, different from the precursor whose synthesis is altered. The incorporation of original precursors into the depsipeptide and in place of the natural precursors leads to the production of novel compounds which are related to the B components of streptogramins and which exhibit advantageous therapeutic properties.

The approach mentioned above (WO 96/01901) has made it possible to obtain microorganism strains which produce mainly, within the B components, isoforms which are naturally produced in the minority. However, it requires supplementing the culture medium with specific precursors which are not present in the natural state in the microorganism strains.

Fundamental biochemical and genetic studies of the biosynthetic pathways for pristinamycin have made it possible to elucidate the origin of the many isoforms observed for the PIs. More particularly, it has been shown that PIB originates from the incorporation into the macrocycle, by the SnbDE peptide synthetase, of L-MMPAPA, a biosynthetic intermediate of L-DMPAPA which is incorporated into the macrocycle of PIA (Blanc et al., Mol. Microbiol (1997), 23(2): 191-202); Thibaut et al., J. Bacteriol. (1997), 179(3): 697-704). Four genes have been identified which are involved in the biosynthesis of L-MMPAPA and L-DMPAPA from chorismate, papA, papB, papC and papM (Blanc et al., 1997).

Figure 3:
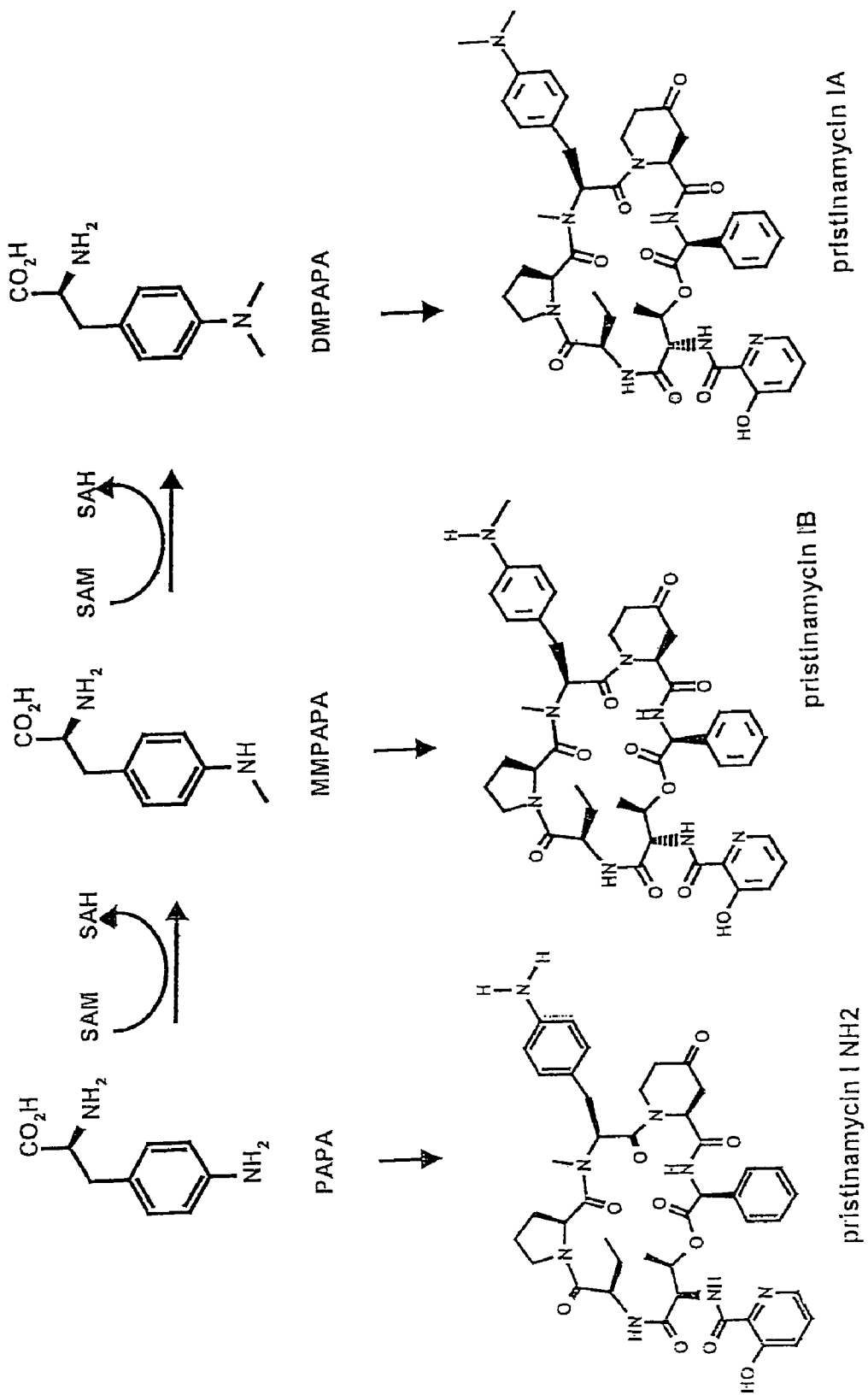

The papM gene encodes a protein which catalyzes the two successive methylation reactions which make it possible to produce L-DMPAPA from 4-amino-L-phenylalanine via L-MMPAPA according to the scheme described in FIG. 3. These two methylation reactions are catalyzed by PapM with very similar kinetic parameters (reaction rate and affinity constants) (Blanc et al., 1997). The sequence of the papM gene of *S. pristinaespiralis* and that of the corresponding polypeptide (4-amino-L-phenylalanine (phenyl N)-methyltransferase) are presented in the sequence SEQ ID No.1.

The present invention is based on the discovery that it is possible to improve the production of certain minor isoforms of the B components of streptogramins by modifying the enzyme activity of the product of the papM gene.

More particularly, the invention is based on the identification of novel variants of the PapM polypeptide which possess a substrate selectivity and/or an improved effectiveness compared to the wild-type polypeptide. The inventors have in fact shown that it is possible to perform mutagenesis on the papM gene such that the corresponding protein is no longer capable of catalyzing the second methylation reaction while at the same time conserving sufficient activity for the first methylation reaction or, at the very least, such that the second methylation reaction is greatly inhibited compared to the first reaction.

The presence of such enzymes in streptogramin-producing microorganisms such as strains of *S. pristinaespiralis* leads to the accumulation of L-MMPAPA and therefore to the preferential production of PIB (FIG. 3). Conversely, it is also possible to perform mutagenesis on the papM gene such that the corresponding protein catalyzes the second methylation reaction with greater efficiency than that of the first methylation reaction; the presence of such enzymes in strains of *S. pristinaespiralis* should lead to the accumulation of L-DMPAPA and therefore to the increased production of PIA.

The invention is also based on the discovery that microorganisms producing an inactive form of the PapM polypeptide or mutants no longer expressing the papM gene allow the accumulation of B components of streptogramins which the wild-type microorganisms are capable of synthesizing naturally but in amounts which are too small to be isolated. Thus, the present invention describes the construction of recombinant strains of *S. pristinaespiralis* which produce mainly a compound of the PI family, called PINH2, that many wild-type strains of *S. pristinaespiralis* are not capable of synthesizing, and which corresponds to the incorporation of a 4-amino-L-phenylalanine in the 4-position of the macrocycle (FIG. 2).

A first subject of the invention concerns a variant of the PapM polypeptide, which exhibits an efficiency of methylation with respect to the methylation substrates which is different (increased or decreased) compared to the efficiency of methylation of the wild-type PapM polypeptide with respect to these same substrates.

The variant of the PapM polypeptide which exhibits [sic] an efficiency of methylation 1 defined by the ratio $Kcat_1/Km_1$ with respect to the methylation substrate 1 and/or an efficiency of methylation 2 defined by the ratio $Kcat_2/Km_2$ with respect to the methylation substrate 2, different from the wild-type PapM polypeptide. Preferably, the PapM variant according to the invention exhibits an efficiency of methylation 1 of L-PAPA to L-MMPAPA defined by the ratio $Kcat_{PAPA}/Km_{PAPA}$ and/or the efficiency of methylation 2 of L-MMPAPA to L-DMPAPA defined by the ratio $Kcat_{MMPAPA}/Km_{MMPAPA}$, different from the efficiency of methylation of the PapM polypeptide presented in SEQ D No. 1.

According to a first embodiment, the PapM variant according to the invention exhibits an efficiency of methylation 1 of L-PAPA to L-MMPAPA which is at least 2 times greater, preferably at least 5 times greater, and more preferably at least 10 times greater, than the efficiency of methylation 2 of L-MMPAPA to L-DMPAPA. Such a variant is more particularly advantageous for producing PIB. Preferably, the variant according to the invention derives from the sequence of the wild-type PapM polypeptide by replacement of one or more amino acids chosen from: the Gly 249 residue (a), the Thr 192 residue (b), and a residue equivalent to (a) or (b) in a homologous polypeptide.

For the purpose of the present invention, the expression "homologous PapM polypeptide" is intended to denote polypeptides originating or derived from bacteria of the *Streptomyces* genus, such as in particular *Streptomyces olivaceus*, *Streptomyces ostreogriseus*, *Streptomyces mitakaensis*, *Streptomyces loïdensis*, *Streptomyces graminofaciens* or *Streptomyces diastaticus*, or other microorganisms the amino acid sequence of which differs from the amino acid sequence SEQ ID No.1 by substitution, deletion and/or insertion of one or more amino acids, and the biological function of which is similar to that of the PapM polypeptide. Such a homologous polypeptide sequence is may be [sic] similar to at least 60% of the sequence SEQ ID No.1, preferably similar to at least 70%, and more preferably similar to at least 80% of the sequence SEQ ID No. 1.

According to a further embodiment, the variant according to the invention derives from the polypeptide sequence SEQ ID No.1 and exhibits at least one substitution, at position 249, of a glycine with a serine.

According to another embodiment, the variant according to the invention derives from the polypeptide sequence SEQ ID No.1 and exhibits at least one substitution, at position 192, of a threonine with an isoleucine.

Finally, according to yet another embodiment, the variant according to the invention derives from the sequence SEQ ID No.1 and exhibits at least one substitution, at position 249, of a glycine with a serine and a substitution, at position 192, of a threonine with an isoleucine.

According to another embodiment, the PapM variant according to the invention exhibits an efficiency of methylation 2 of L-MMPAPA to L-DMPAPA which is at least 2 times greater, preferably at least 5 times greater, and more preferably at least 10 times greater, than the efficiency of methylation 1 of L-PAPA to L-MMPAPA. Such a variant is more particularly advantageous for increasing the production of PIA.

The invention also relates to a nucleic acid encoding a variant of the polypeptide as defined above. It is preferably a nucleic acid derived by mutation from the nucleotide sequence presented in SEQ ID No.1 or the sequences derived due to the degeneracy of the genetic code. Advantageously, the nucleic acid according to the invention comprises at least one missense mutation upstream of the NPPY motif located at positions 193 to 196, and preferably this missense mutation leads to a non-conservative amino acid change, such as, for example, the substitution of a cytosine at position 658 with a thymine (C658T) (mutated allele 66). Another advantageous embodiment concerns a nucleic acid which comprises at least one substitution of a guanine at position 828 with an adenine (G828A) (mutated allele 49). Finally, another more particularly advantageous form lies in a nucleic acid which comprises at least one substitution of guanine at position 828 with an adenine (G828A) and at least one substitution of a cytosine at position 658 with a thymine (C658T) (mutated allele 49/66).

A subject of the invention is also the use of a nucleic acid as defined above, for modifying the proportion of the B component isoforms in a streptogramin-producing strain. As streptogramin-producing strains which can be used in the context of the invention, mention may particularly be made of the *Streptomyces olivaceus, Streptomyces ostreogriseus, Streptomyces mitakaensis, Streptomyces loïdensis, Streptomyces graminofaciens, Streptomyces diastaticus* etc. strains. The nucleic acids encoding a PapM variant which exhibits an efficiency of methylation 1 of PAPA to MMPAPA which is at least 2 times greater, preferably at least 5 times greater, and more preferably at least 10 times greater, than the efficiency of methylation 2 of MMPAPA to DMPAPA are more particularly of use for producing PIB when they are expressed in a strain of *S. pristinaespiralis*. The nucleic acids encoding a PapM variant which exhibits an efficiency of methylation 2 of MMPAPA to DMPAPA which is at least 2 times greater, preferably at least 5 times greater, and more preferably at least 10 times greater, than the efficiency of methylation 1 of PAPA to MMPAPA are more particularly of use for producing PIA when they are expressed in a strain of *S. pristinaespiralis*.

A subject of the invention is also any recombinant DNA comprising a nucleic acid as defined above.

Figure 11:
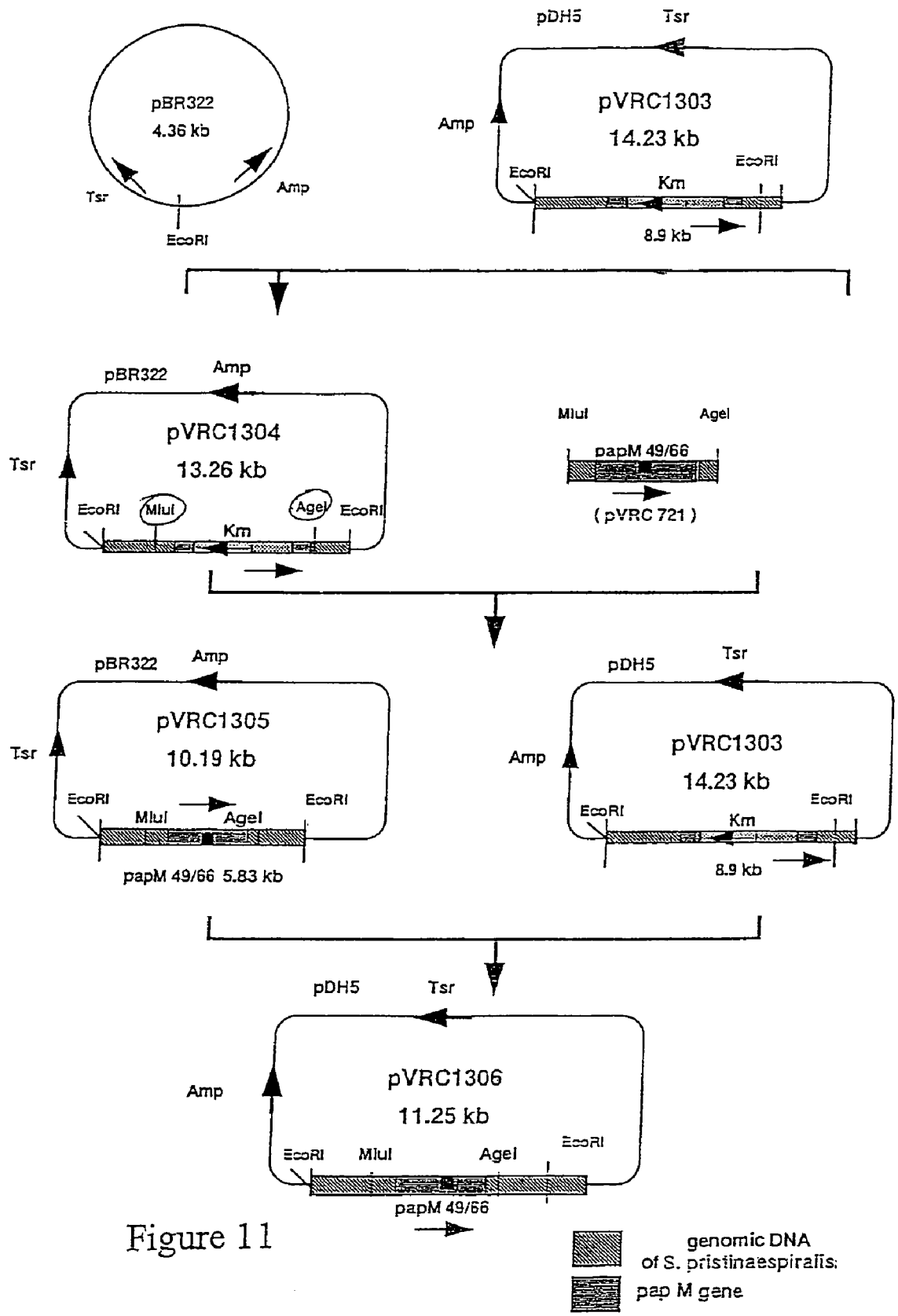

The invention also relates to any expression vector which replicates autonomously and/or which integrates, comprising a nucleic acid or a recombinant DNA as defined above, such as in particular a vector comprising all or part of the vector pVRC1306 represented in FIG. 11.

A subject of the invention is also the host cells containing a nucleic acid and/or a recombinant DNA and/or an expression vector as defined above. The host cells according to the invention can be both eukaryotic and prokaryotic cells. Among the eukaryotic cells which are suitable, mention may be made of animal cells, yeast or fungi. In particular, as regards yeast, mention may be made of yeast of the *Saccharomyces, Kluyveromyces, Pichia, Schwanniomyces* or *Hansenula* genus. As regards animal cells, mention may be made of COS, CHO and C127 cells, *Xenopus* eggs, etc. Among fungi, mention may be made more particularly of *Micromonospora, Aspergillus* ssp. or *Trichoderma* ssp. As prokaryotic cells, use if preferable made of the following bacteria: *Actinomycetes*, and in particular *Streptomyces, E. coli* (example 7), *Bacillus*. Preferentially, the recombinant cells of the invention are chosen from streptogramin-producing cells and in particular *Streptomyces olivaceus, Streptomyces ostreogriseus, Streptomyces mitakaensis, Streptomyces loïdensis, Streptomyces graminofaciens* and *Streptomyces diastaticus*. The recombinant cells of the invention can be obtained by any method for introducing a foreign nucleotide sequence into a cell. It may in particular be transformation, electroporation, conjugation, protoplast fusion, or any other technique known to those skilled in the art.

A subject of the invention is also a method for producing a variant of the PapM polypeptide according to the invention, wherein a host cell as defined above is cultured and the polypeptide produced is recovered.

The invention also relates to the use of a host cell as defined above and expressing a variant of the PapM polypeptide according to the invention, in a bioconversion reaction. In particular, these cells can make it possible to convert aromatic amines to monomethylated amines, in particular 4-amino-L-phenylalanine to 4-methylamino-L-phenylalanine. These bioconversions can take place either using whole cells or using acellular extracts of said cells.

Another subject of the invention concerns a method for producing a B component of streptogramins, wherein:
the papM gene is inactivated in a streptogramin-producing or potentially streptogramin-producing strain, and one or more copies of a nucleic acid encoding a papM variant as defined above are introduced,
said strain is cultured under conditions for producing streptogramins, and
the B component of streptogramins produced is recovered.

Preferentially, the streptogramin-producing strain is a pristinamycin-producing strain derived from *S. pristinaespiralis*, and more preferably it is derived from the strain *S. pristinaespiralis* SP92 or from *S. pristinaespiralis* ATCC25486. It can also be chosen from the following strains: *Streptomyces olivaceus* ATCC12019, *Streptomyces ostreogriseus* ATCC27455, *Streptomyces mitakaensis* ATCC15297, *Streptomyces loïdensis* ATCC11415, *Streptomyces graminofaciens* and *Streptomyces diastaticus*.

Advantageously, the streptogramin-producing strain is a strain which produces a small or undetectable amount of A components of streptogramins. As strains which do not produce A components of streptogramins, mention may in particular be made of the strain *S. osteogriseus* Pr4Q031/CBS 142.93 described in application WO 93/20182. As regards the examples of strains of S. pristinaespiralis which do not produce A components, mention may be made of the strain SP213 derived from SP92 (Blanc et al., 1994) after chemical mutagenesis, or the strain S. pristinaespiralis Pr4R31 (deposited as CBS182.92) described in application WO 93/20182; the strains SP213 and Pr4R31 produce specifically pristinamycins P1 and no longer produce a detectable amount of pristinamycins PII (A components).

According to a preferred variant, the introduction of the nucleic acid encoding a PapM variant according to the invention is carried out by replacing the wild-type form of the papM gene. Depending on the variant expressed by the nucleic acid introduced, it is possible to promote the production of various B components of streptogramins. Thus, a strain of S. pristinaespiralis expressing a variant with a $Kcat_{PAPA} \cdot Km_{MMPAPA}/Kcat_{MMPAP} \cdot Km_{PAPA}$ ratio which is increased compared to the wild-type polypeptide leads to the preferential production of PIB. Conversely, a variant exhibiting a decrease in this ratio should make it possible to obtain an increased production of PIA. Preferentially, for the production of PIB, the strain of S. pristinaespiralis comprises a papM gene exhibiting at least the mutation (G828A) or the mutation (C658T) or the double mutation (C828A)(C658T).

The invention also relates to a method for producing PINH2, wherein a strain is used in which the wild-type form of the papM gene of S. pristinaespiralis is inactivated and/or replaced with a nucleic acid encoding an inactive form of the PapM polypeptide.

A subject of the invention is also a mutant strain of S. pristinaespiralis, which comprises a nucleic acid encoding a variant of the PapM polypeptide according to the invention. Such a strain can be obtained in particular by transformation of a recombinant strain in which the wild-type papM gene has been disrupted and replaced with a cassette Ω-Km (cf. example 8) with a suicide plasmid which allows exchange of this cassette with one of the mutated alleles of papM. By way of illustration, the invention describes the strain S. pristinaespiralis SP217 comprising a nucleic acid carrying the mutation C658T (mutant allele 66) or the strain S. pristinaespiralis SP218 comprising the double mutation C658T and G828A (mutant allele 49/66). These mutations were introduced into the strain S. pristinaespiralis SP213 disrupted beforehand in the papM gene, replaced with a cassette Ω-Km. An identical approach enabled the construction of the strain S. pristinaespiralis SP101 with the introduction of the mutant allele 66 into the strain SP92. The strains S. pristinaespiralis SP101, SP218 and SP217, which synthesize a papM variant according to the invention, produce mainly PIB.

A subject of the invention is also the use of a strain of S. pristinaespiralis for producing PINH2. Such a strain is in particular illustrated by the strain SP216 which derives from the strain SP213 after inactivation of the papM gene and which produces mainly PINH2.

The invention also relates to a method for selecting the variants of the PapM polypeptide or of a polypeptide encoded by a homologous gene, according to which:
  a chemical mutagenesis step is carried out on the papM gene or a homologous gene cloned into a plasmid,
  a library is prepared by transforming a recipient strain with the plasmids on which mutagenesis was performed in step (a),
  the clones which exhibit a methylation activity such that the ratio "r" of the amounts of methylation substrate transformed per unit of time under initial rate conditions, with r=substrate 1/(substrate 1+substrate 2), is increased by at least 20% compared to the wild-type polypeptide, and preferably greater than or equal to 0.6, are selected.

In this regard, the present invention shows how it is possible to perform chemical mutagenesis with hydroxylamine, in vitro, on the papM gene cloned into a plasmid, so as to constitute a library of mutants and to select, from this library, using miniaturized enzymatic screening, the Escherichia coli clones which express the mutated papM genes for which the corresponding proteins have the catalytic properties described above and which exhibit a ratio "r" as defined above, greater than or equal to 0.6.

The present invention is illustrated using the following examples which should be considered to be nonlimiting illustrations.

FIGURE LEGENDS

Figure 5:
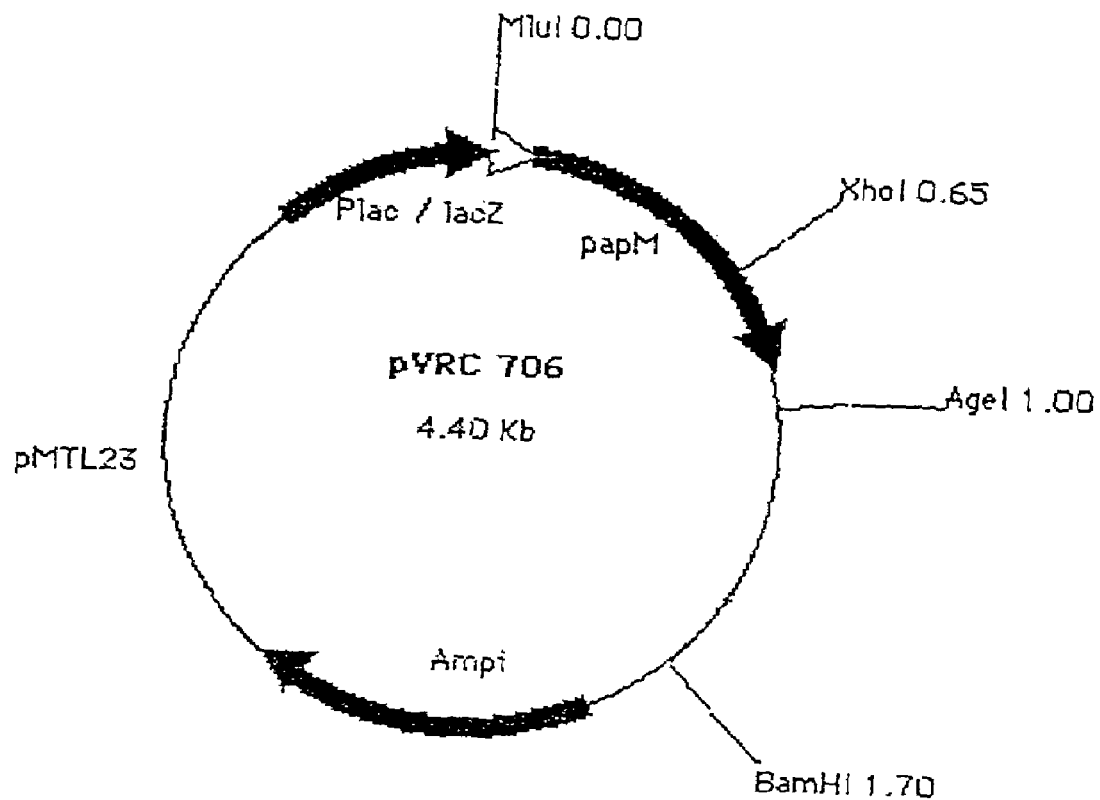
Figure 6:
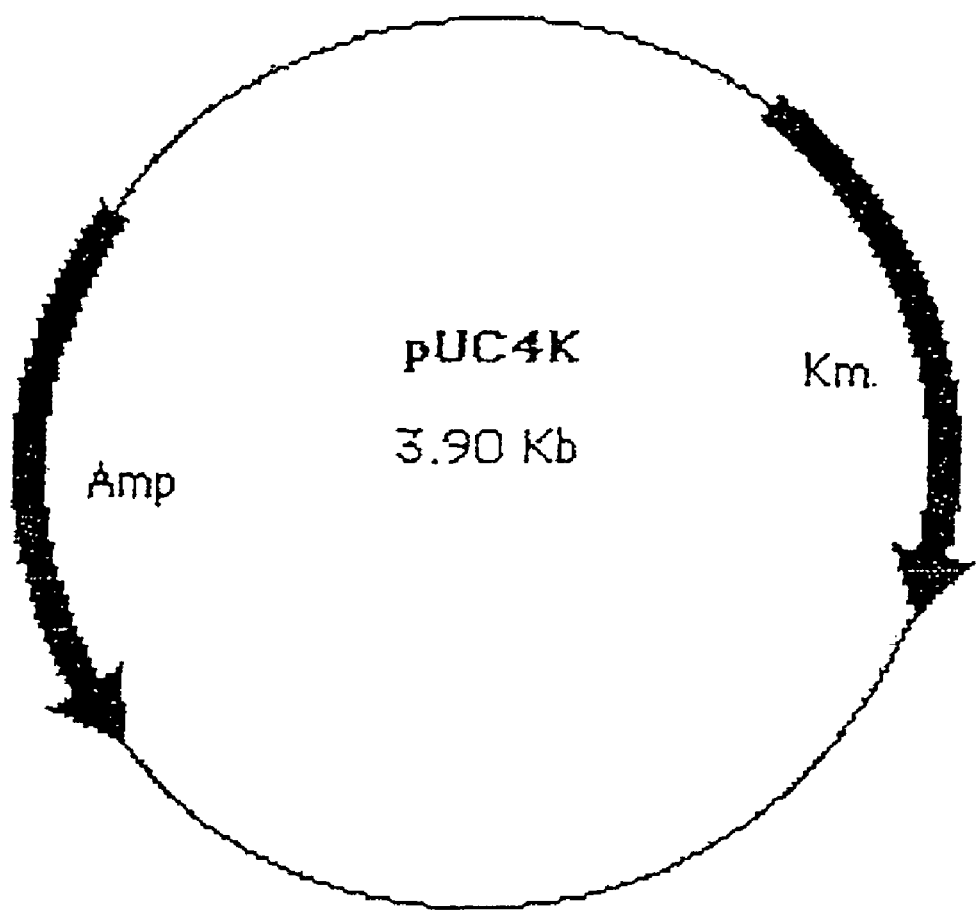
Figure 8:
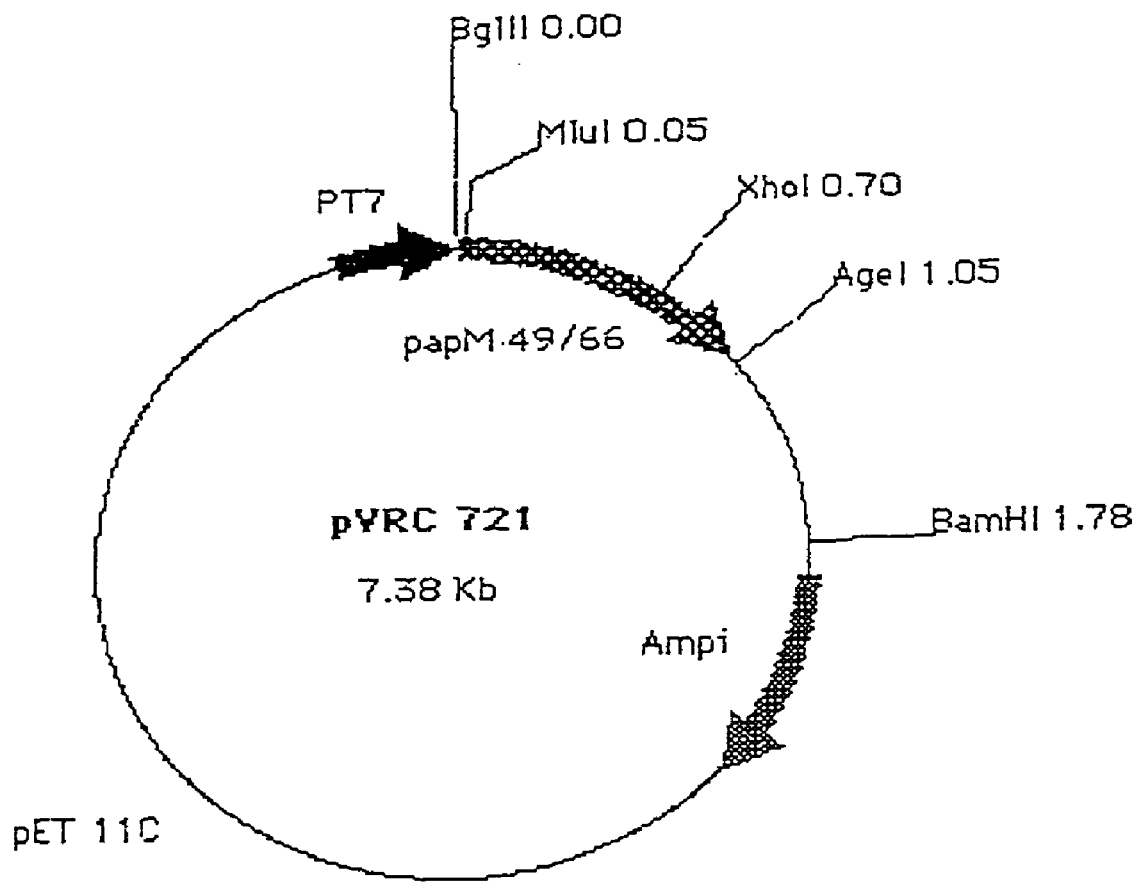
Figure 9:
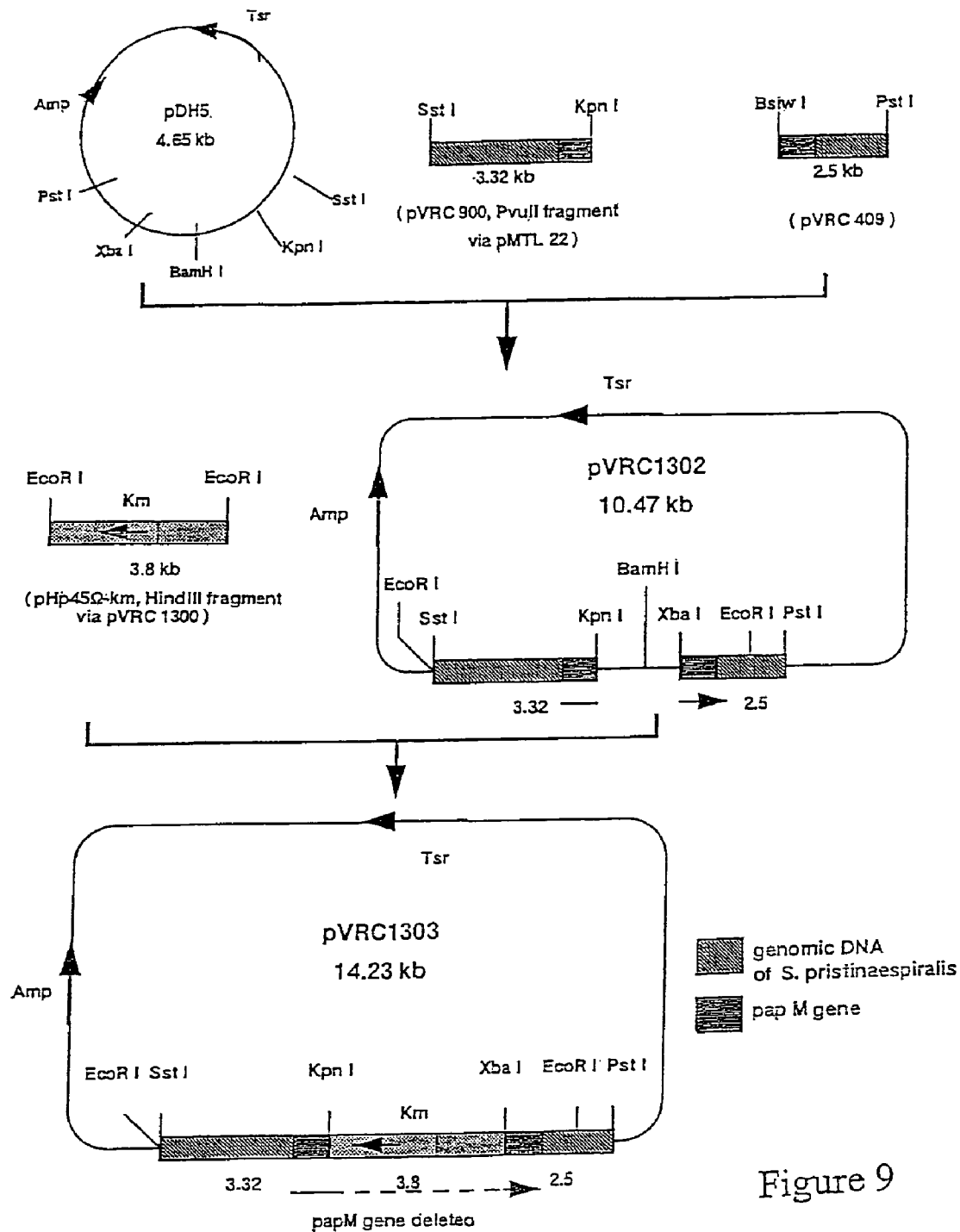
Figure 10:
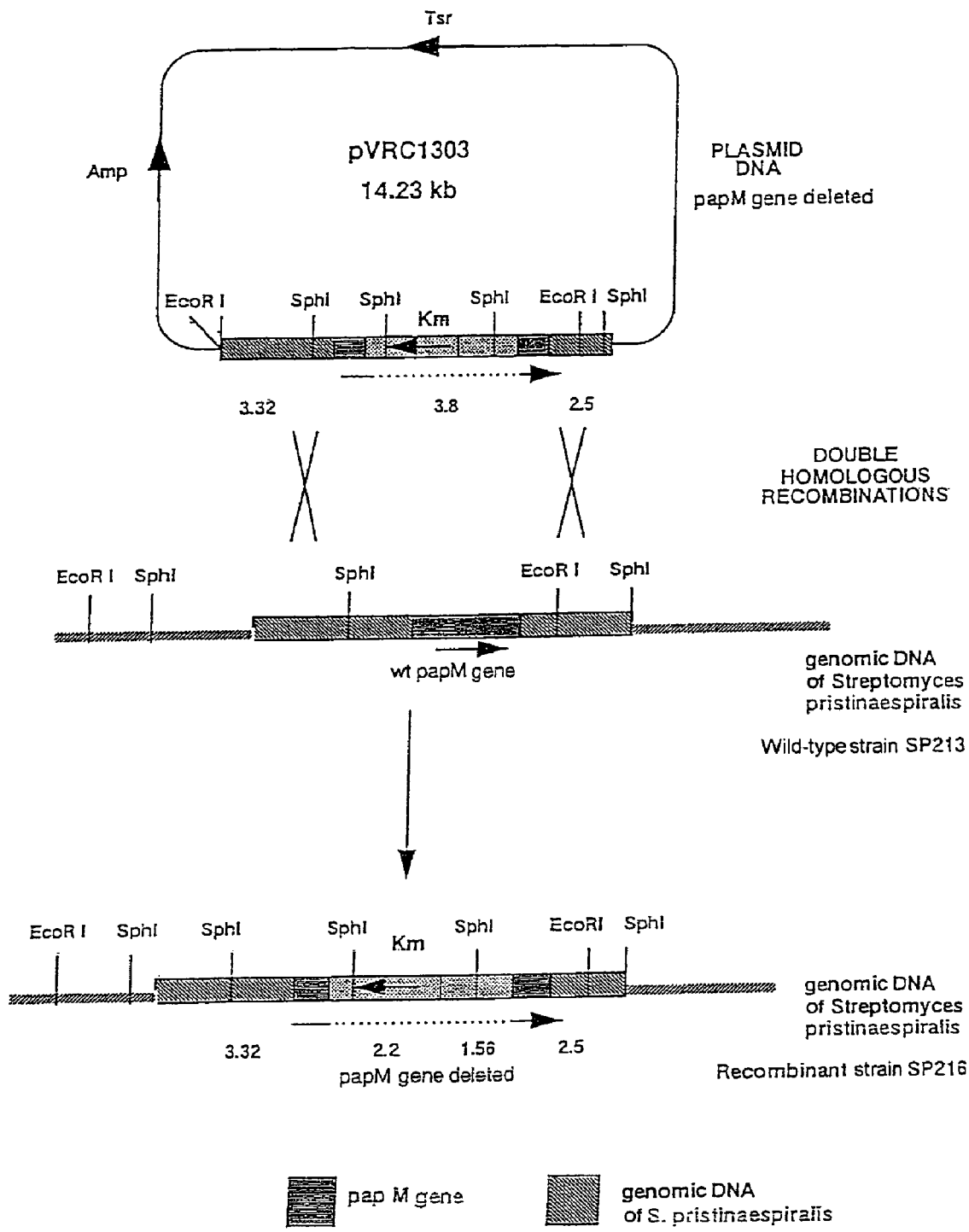
Figure 12:
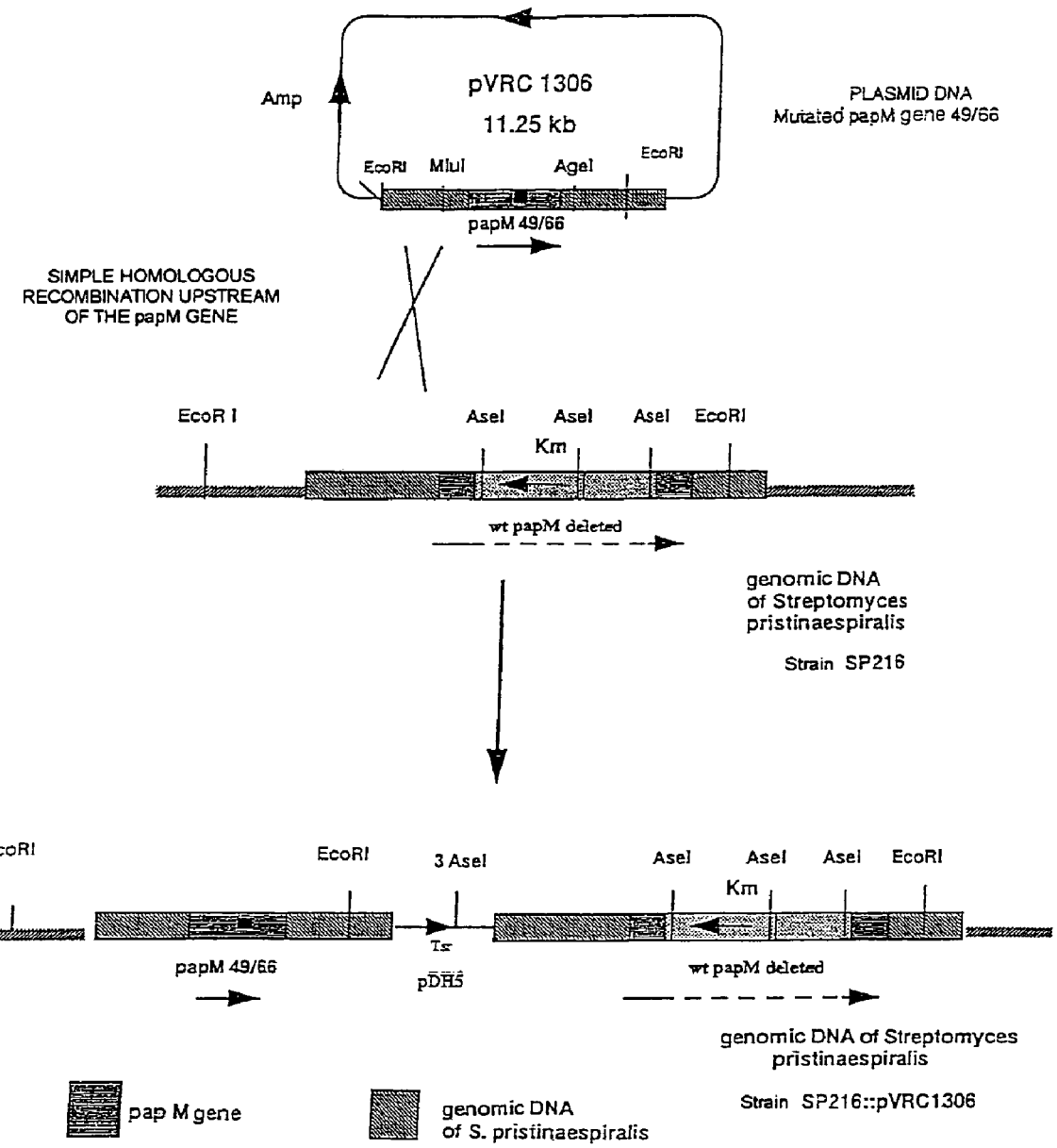
Figure 13:
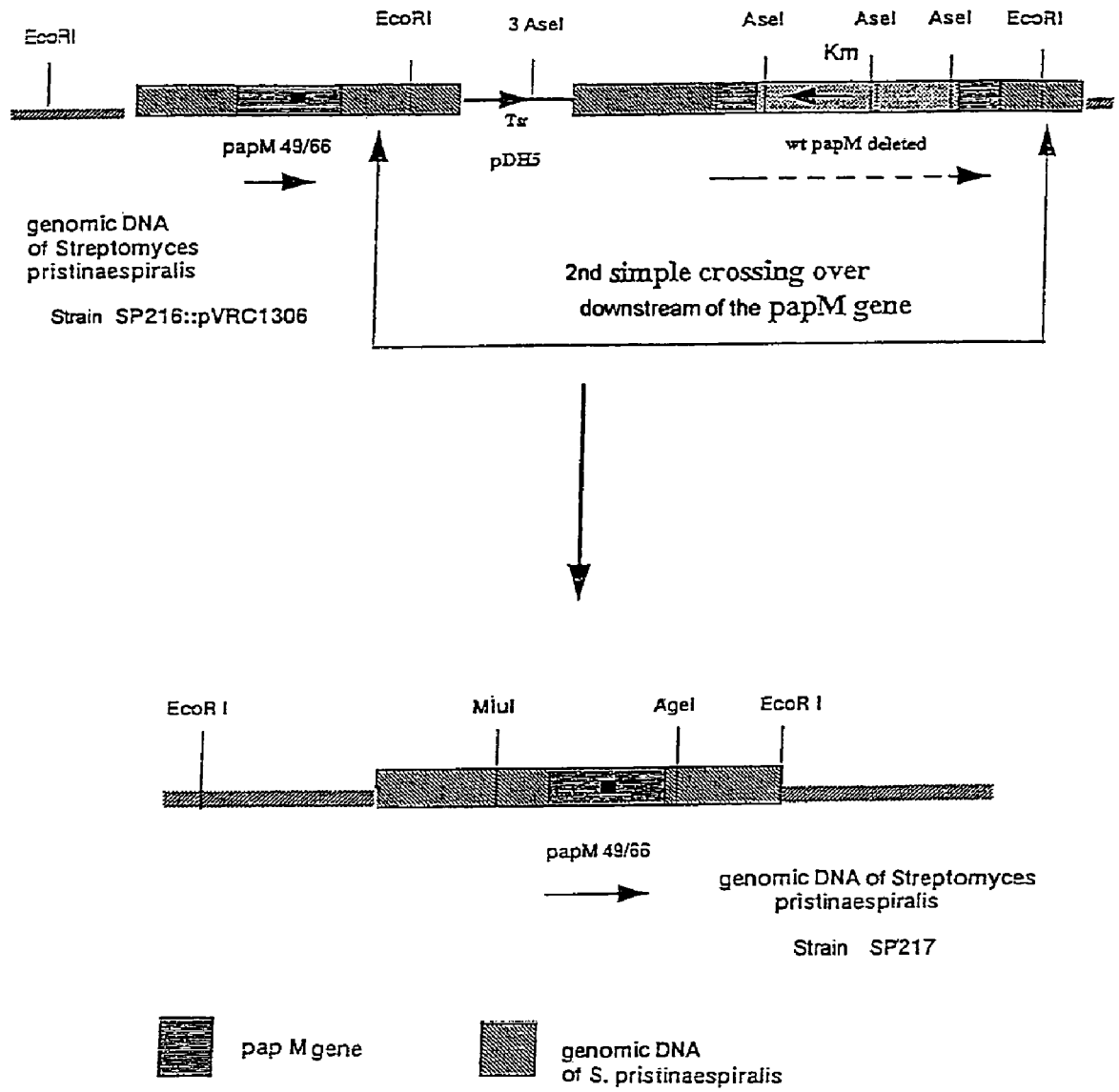

FIG. 1: Example of structure of pristinamycins II.
FIG. 2: Example of structure of pristinamycins I.
FIG. 3: Biosynthetic pathway for MMPAPA and DMPAPA, respective precursors of PIB and PIA.
FIG. 4: Principle of the enzyme assay used to screen the PapM mutants: labeling by simultaneous methylation of MMPAPA and of DMPAPA from, respectively, PAPA and MMPAPA, in the presence of [$^{14}$C-Me]-SAM.
FIG. 5: Representation of the plasmid pVRC706.
FIG. 6: Representation of the plasmid pUC4K.
FIG. 7: Sequence and translation of the wild-type papM gene (coding sequence84-962 of SEQ ID NO: 1). Positions of the mutations identified for the mutated clones 49 and 66.
FIG. 8: Representation of the plasmid pVRC721.
FIG. 9: Strategy for constructing the plasmid pVRC1303.
FIG. 10: Representation of the case of double crossing over between the plasmid pVRC1303 and the chromosome of S. pristinaespiralis. Chromosomal structure of the recombinant strains.
FIG. 11: Strategy for constructing pVRC1306.
FIG. 12: Representation of the case of single crossing over selected between the plasmid pVRC1306 and the chromosome of the recombinant strain SP216.
FIG. 13: Representation of the case of a second recombination event producing a recombinant strain showing one of the mutated alleles of the papM gene.

BIBLIOGRAPHY

Blanc et al., (1994) WO 94/08014
Blanc et al., (1995), J. Bacteriol. 177(18): 5206-14
Blanc et al., Mol. Microbiol (1997), 23(2): 191-202
Chambers et al. (1988) Gene. Aug 15; 68(1): 139-49
Cocito C. G. (1979) *Microbiol. Rev.*, 43: 145-198
Cocito C. G. (1983) *In Antibiotics*, 6: (Ed. F. E. Hahn), 296-332
Dessen P. C., Fondrat C., Vanelcien C. and Mugnier C. (1990) *Comp. Appl. in Biosciences*, 6: 355-356
Di Giambattista M., Chinali G. and Cocito C. G. (1989) *J. Antim. Chemother.*, 24: 485-507
Fellay et al., (1987) Gene. 52(2-3): 147-54
Hanahan et al. (1990) PNAS USA 87, pp 4645-4649 (1990)
Hillemann D., Pülher A. and Wohlleben W. (1991) *Nucl. Acids Res.*, 19: 727-731
Hopwood D. A., Bibb M. J., Chater K. F., Kieser T., Bruton C. J., Kieser H. M., Lydiate D. J., Smith C. P., Ward J. M. and Scrempf H. (1985) *A laboratory manual.*, The John Innes Foundation, Norwich, England
Humphreys et al., (1976) Mol Gen Genet. Apr 23; 145(1): 101-8

Maniatis T., Fritsh E. F. and Sambrook J. (1989) Molecular cloning: a laboratory manual. *Cold Spring Harbor, N. Y.*
Messing J., Crea R. and Seeburg P. H. (1981) *Nucleic Acids Res.,* 9: 309
Schluckebier et al. (1995) Gene. May 19; 157(1-2): 131-4
Thibaut et al., (1997) J. Bacteriol. 179(3): 697-704
Veira and Messing, Gene. 1982 Oct.; 19(3): 259-68

EXAMPLES

Example 1

Methodology and Protocol for Enzymatic Screening

This example illustrates the screening of mutated forms of the PapM enzyme exhibiting new kinetic characteristics, using a population of enzymes derived from mutagenic treatment with hydroxylamine (cf. examples 2 and 3). In particular, this example illustrates the production of mutated forms of PapM having a modified selectivity for the two natural substrates for this enzyme.

1.1. Methodology

The papM methylase has been previously cloned, purified and characterized (Blanc. et al., 1994; Blanc et al., 1997). PapM is a bifunctional enzyme which catalyzes both the N-methylation of L-PAPA to L-MMPAPA and that of L-MMPAPA to L-DMPAPA (see FIG. 4).

L-PAPA and L-MMPAPA are two competitive substrates for PapM, having respective Michaelis constants (Km) of 240 and 530 µM, and for which the maximum velocity of PapM (Vmax) is respectively 55 and 71 µmol per hour and per mg of PapM (Blanc et al., 1997).

The ratio of the respective rates V1 and V2 of methylation of L-PAPA and of L-MMPAPA is dependent on the kinetic parameters of PapM (Km1 and Vmax1 for L-PAPA, Km2 and Vmax2 for L-MMPAPA), and is also dependent on the respective concentrations S1 and S2 of L-PAPA and of L-MMPAPA, according to the formula:

$$V1/V2=(Vmax1/Km1)[S1]/(Vmax2/Km2)[S2]$$

Simultaneous measurement of the two rates of methylation V1 and V2 at fixed concentrations of S1 and S2 makes it possible to determine the ratio of the kinetic constants of PapM for L-PAPA and L-MMPAPA. This ratio is independent of the amount of PapM used in the assay. When the selectivity of the mutated PapM enzyme increases for L-PAPA, the ratio V1/V2 should increase and, conversely, this ratio should decrease when the mutated PapM enzyme preferentially methylates L-MMPAPA.

Finally, in order to avoid small variations in Km and to, on the contrary, promote either large variations in Km or modifications in the Vmax values, the concentrations of L-PAPA and L-MMPAPA are fixed at approximately 6 times the Km in order to be under conditions of saturation. Under such conditions, with the wild-type PapM enzyme, the rate of methylation 1 and the rate of methylation 2 are virtually equal.

The simultaneous assaying of the two methylation activities of PapM is described in example 7.1. This assaying of the methylase activities of PapM is carried out in the presence of 1.5 mM L-PAPA, 3 mM L-MMPAPA and 70 µl SAM.

1.2. Screening of the Population of Mutated PapM Enzymes

The 96-well plates of the library of *E. coli* clones producing the mutated PapM enzymes, prepared as described in example 3, are thawed at 23° C. Next, 25 µl of mixture A are added to the 200 µl of the culture on LB medium contained in each well. Mixture A is obtained by adding successively (1) 3 ml of 50 mM Bis-Tris-Propane buffer, pH 10, in which have been dissolved 12 mg of L-PAPA, and 71 mg of (DL-)-MMPAPA in dihydrochloride form and prepared as described in WO 96/01901-A1, (2) 0.7 ml of 4 mM SAM in water, (3) 0.7 ml of [$^{14}$C-Me]-SAM at 25 µCi/ml and 60 mCi/mmol (AMERSHAM), (4) 0.6 ml of 100 mM Bis-Tris-Propane buffer, pH 6.8, and (5) 56 mg of the disodium salt of EDTA. The amounts are given for the preparation of a 5 ml volume of mixture A. The plate is then sealed with an adhesive film, and then incubated at 27° C. for 2 hours. The reaction is stopped with 40 µl of a stop solution. The stop solution (for a volume of 4 ml) is obtained by mixing 2.2 ml of a 24 mg/ml sodium heptanesulfonate solution in water with 1.8 ml of concentrated hydrochloric acid. After centrifugation of the plates at 3 000 g for 5 min, approximately 100 µl of the supernatant of each well are analyzed by HPLC in the system described in example 7.1.

For each well, the respective areas A1 and A2 of the MMPAPA and DMPAPA peaks derived from recording the radiochemical detection are integrated. A ratio r is then calculated in the following way:

$$r=A1/(A1+A2)$$

In the case of the wild-type PapM methylase, r=0.50±0.05.

The threshold of the ratio r which is fixed for a mutated PapM enzyme which is significantly more active for the methylation 1 than the methylation 2 is approximately 0.60.

Example 2

Mutagenesis of the papM Gene with Hydroxylamine

This example illustrates the mutagenesis of the papM gene using a plasmid DNA of *Streptomyces* cloned into a plasmid which can replicate in *E. coli*.

2.1. Choice of the Mutagenic Agent

Chemical mutagenesis was carried out using hydroxylamine (NH$_2$OH), which binds specifically to the cytosine residues so as to form N4-hydroxy-cytosines which are then capable of pairing with the adenine residues. The hydroxylamine therefore causes G:C>A:T transitions. The choice of this mutagenic agent is particularly advantageous for performing mutations of GC-rich DNAs, such as the DNA of *Streptomyces* which contains 70 to 75% of GC residues.

2.2. Choice of the Plasmids on which to Perform Mutagenesis

The mutagenesis was carried out simultaneously on two different plasmids, the plasmid pVRC706 and the plasmid pUC4K.

The plasmid pVRC706 (FIG. 5) is a derivative of pMTL23 (Chambers et al., 1988) into which the 1.7 kb MluI-StuI fragment derived from the plasmid pVRC409 carrying the papM gene on which the mutagenesis is to be performed (Blanc et al., 1994; Blanc et al., 1997) has been cloned between the unique MluI and BamHI sites (the end cleaved by BamHI having been blunt-ended by the action of the Klenow enzyme according to the protocol of Sambrook et al., (1989)). Cloning of the StuI end into the BamHI site of pMTL23, filled using the Klenow enzyme, makes it possible to reconstitute the BamHI site which can be re-used during subsequent cloning. The cloning at the MluI site makes it possible to obtain an in-phase fusion between the first 32 amino acids of the β-galactosidase encoded by the lacZ gene of the plasmid pMTL23 and the last 11 amino acids of the papB gene located upstream of the papM gene; this preserves the translational coupling which appears to exist between these two genes in view of the nucleotide sequence (Blanc et al., 1994). In this construct, the expression of the papM gene is controlled by the Plac promoter of the lacZ gene which is inducible by adding 1 mM of IPTG. It has previously been shown that such an expression system makes it possible to produce, in *E. coli*, the PapM methylase in the form of an active and soluble protein representing approximately 0.5% of the total proteins (Blanc et al., 1994).

The plasmid pUC4K (FIG. 6) is a derivative of the vector pUC4 carrying the two genes which confer resistance to ampicillin and to kanamycin (Vieira and Messing, 1982). This plasmid was chosen as a mutagenesis control for the following reasons: (1) its size (3.9 kb) is close to the plasmid pVRC706 (4.4 kb), (2) the two plasmids pUC4K and pVRC706 have a structure and properties which are very close since they both derive from vectors of the pUC series, and (3) the presence of two resistance genes, ampP and kanR, carried by pUC4K makes it possible to easily calculate the percentage of clones which have undergone mutagenesis in one of these genes by counting the clones sensitive to the chosen antibiotic.

2.3. Mutagenesis Protocol

Two mutageneses with hydroxylamine were carried out according to the protocol of Humprey et al., (1976), varying the incubation temperature: 80° C. and 85° C.: 5 mg of plasmid DNA purified on a cesium chloride gradient are brought into contact with 0.4 M of hydroxylamine (pH 6) in a final volume of 100 ml for 35 minutes at the desired temperature (80° C. or 85° C.) in a buffer containing 0.05 M of sodium phosphate and 0.5 mM of EDTA. The mutagenesis reaction is stopped by adding 100 ml of buffer containing 0.1 M of sodium phosphate and 1 mM of EDTA, and the hydroxylamine is removed with eight successive dialysis baths against 2 liters of TES buffer (10 mM Tris, pH 7.5, 1 mM EDTA and 100 mM NaCl). The DNA thus treated is precipitated by adding a 1/10 volume of 3M sodium acetate (pH 8) and 2.5 volumes of 95% ethanol. The DNA pellet is rinsed, dried, and then taken up in 100 µl of TE buffer (10 mM Tris-HCl and 1 mM EDTA, pH 7.5). For each plasmid, a control for the mutagenesis reaction was performed at the temperature studied, in the absence of hydroxylamine.

2.4. Preparation of the *E. coli* Strain Receiving the Plasmids on which Mutagenesis was Performed The *E. coli* strain DH5α (supE44 DlacU169 (f80lacZDM15) hsdR17 recA1 endA1 gyrA96 thi-1 re1A1), (Hanahan, 1990) was used to evaluate the mutagenesis after transformation with the plasmids pVRC706 and pUCK4 on which mutagenesis was performed according to the protocol described above.

The *E. coli* DH5α cells competent for transformation by electroporation were prepared according to the following protocol: a 1 liter culture in LB medium is prepared at 37° C. until the O.D. (at 600 nm) reaches 0.5 to 0.8. The cells are then placed on ice for 30 minutes to stop their growth, and then centrifuged at 4° C. at 4 000 g for 15 min. The cell pellet is successively rinsed with 1 liter of cold sterile water, 0.5 liter of cold water and 20 ml of a cold solution containing 10% of glycerol. After each rinse, the cells are centrifuged at 4° C. at 4 000 g for 15 min. Finally, the cell pellet is taken up in 2 ml of 10% strength glycerol. The cells thus prepared can be immediately electroporated or else frozen and stored at −80° C. in the form of 40 ml aliquots with a view to subsequent use. The efficiency of transformation of electrocompetent cells is of the order of $10^9$ colonies/µg of pUC18 plasmid DNA.

The *E. coli* DH5α cells thus prepared were electroporated with the equivalent of 5 ng of test plasmid. To do this, 40 µl of electrocompetent cells are brought into contact, for 1 min at 4° C., with 1 to 2 µl of a solution containing 5 ng of plasmid DNA. The electroporator (Bio-Rad) is set for a pulse of 25 mF and 2500 V. The resistance of the pulse controller is set at 200 Ω. The cell/DNA mixture is placed in an electroporation cuvette with a 0.2 cm width and the electric pulse is applied. A pulse time of 4.5 to 5 ms is conventionally obtained. After the pulse, 1 ml of SOC medium (2% bacto-agar, 10 mM NaCl, 2.5 mM KCl, 10 mM $MgCl_2$, 10 mM $MgSO_4$, 20 mM glucose) is rapidly added to the cells and the entire mixture is transferred into a 5 ml polypropylene tube, which is incubated for 1 hour at 37° C. This step allows the cells to recover and to begin expressing the resistance gene(s) present on the plasmids which have penetrated the cells. At the end of the incubation, the cell culture is suitably diluted (the dilution factors are conventionally from $10^{-1}$ to $10^{-4}$) and the transformed colonies are selected on solid LB medium containing the selection antibiotic (50 µg/ml of ampicillin or 50 µg/ml of kanamycin).

2.5. Evaluation of the Mutagenesis and Determination of the Selected Temperature Condition The two mutagenesis temperature conditions tested were evaluated according to the following two criteria: firstly, the ability of the plasmids on which mutagenesis is performed to transform an *E. coli* strain and, secondly, the percentage of *E. coli* clones transformed with the pUC4K plasmids on which mutagenesis is performed, which have lost one of the two resistances encoded by the plasmids.

For the two plasmids pVRC706 and pUCK4, the ability of the plasmids on which mutagenesis with hydroxylamine was performed, to transform the *E. coli* strain DH5α, was measured. This ability was compared to that of the plasmids on which mutagenesis was not performed, prepared as a control for the incubation temperature, in the absence of hydroxylamine. Specifically, the action of the hydroxylamine should engender lethal mutations in the plasmids, and more particularly in the resistance genes allowing selection of the recombinant clones, and also in the regions carrying the origin of replication. It can therefore be considered that the more efficient the mutagenesis treatment, the greater the loss of ability to transform of a plasmid. The abilities to transform of the two plasmids on which mutagenesis was performed, expressed as % of the ability of the control plasmids on which mutagenesis was not performed, are indicated in the table below.

TABLE 1

|  | pVRC706 | | pUC4K | |
| --- | --- | --- | --- | --- |
|  | 80° C. | 85° C. | 80° C. | 85° C. |
| Ampicillin | 12.5 | 1.5 | 14 | 1.5 |
| Kanamycin | — | — | 16 | 0.3 |

These results clearly indicate that the mutagenesis at 85° C. is clearly more efficient for the two plasmids pVRC706 and pUC4K since it alters statistically 10 times more plasmid entities, such that only 1.5% of the plasmids are still capable of transforming electrocompetent *E. coli* DH5α cells, of replicating and of conferring ampicillin resistance on the resulting clones. In addition, the results observed with pUC4K are very homogeneous whatever the selection chosen, ($Ampi^R$) or ($Kana^R$), which indicates that the action of the hydroxylamine occurred homogeneously in the regions essential to the expression of these two resistances.

The second criterion for evaluation consisted in calculating, for the plasmids pUC4K on which mutagenesis was performed, the % of clones sensitive to kanamycin ($Kana^S$) among the clones resistant to ampicillin ($Ampi^R$), and vice versa. These percentages reflect the frequency of the mutations which have occurred, under the effect of hydroxylamine, in the resistance genes under consideration (ampR or kanR) and which have disturbed their expression either by complete blocking (stopping transcription or translation), or by leading to the synthesis of a truncated and/or inactive protein.

To estimate these percentages, 200 (Kana$^R$) or (Ampi$^R$) clones chosen from the clones obtained after transformation of electrocompetent cells of the *E. coli* strain DH5α with the plasmids pUC4K on which mutagenesis was or was not performed, were subcultured on solid LB medium containing respectively ampicillin or kanamycin. The clones sensitive to one of the two antibiotics were counted after 24 h of growth. The percentages of clones sensitive to ampicillin or to kanamycin among the clones transformed with the plasmids pUC4K on which mutagenesis with hydroxylamine was or was not performed are given in the table below.

TABLE 2

|  | pUC4K + hydroxylamine | | pUC4K on which mutagenesis was not performed | |
|---|---|---|---|---|
|  | 80° C. | 85° C. | 80° C. | 85° C. |
| (Ampi$^S$)/(Kana$^R$) | 1.3 | 3.2 | 0 | 0 |
| (Kana$^S$)/(Ampi$^R$) | 1.5 | 6 | 0 | 0 |

The results make it possible to conclude that only the treatment with hydroxylamine clearly engendered mutations affecting the expression of one of the two resistance genes of pUC4K. They also make it possible to conclude that the mutagenesis carried out at 85° C. was 3 to 4 times more efficient for the two resistance genes of the plasmid pUC4K than the mutagenesis performed at 80° C. Finally, these samples show that the action of the hydroxylamine was relatively homogeneous for the two resistance genes ampR and KanR.

It can therefore reasonably be supposed that the action of the hydroxylamine took place on all of the two plasmids pUC4K and pVRC706 and that the mutagenesis formed at 85° C. is probably that which most affected the papM genes carried by the plasmids pVRC706. This comparison of the mutagenesis conditions led us to select, for the remainder of the study, only the clones resulting from the transformation of the electrocompetent cells of the *E. coli* strain DH5α with the plasmids pVRC706 derived from the mutagenesis with hydroxylamine carried out at 85° C.

Example 3

Constitution and Exploitation of a Library of *E. coli* DH5α Harboring Plasmids pVRC706

This example illustrates the construction and the exploitation of a library of 6 000 clones of the *E. coli* strain DH5α harboring plasmids which have undergone chemical mutagenesis with hydroxylamine carried out at 85° C.

In the case of the mutagenesis with hydroxylamine carried out at 85° C. on the plasmids pVRC706 carrying the papM gene as described above, it is possible to assess, putting forward the hypothesis that the action of the hydroxylamine was general on all the plasmids pVRC706 (cf. example 2), that a library of 6 000 *E. coli* clones harboring these plasmids represents a library of mutants in which a certain percentage of the clones express a mutated papM gene. Analysis of the 6 000 clones of the library by simultaneously assaying the two methylation activities catalyzed by the corresponding PapM proteins confirms this hypothesis (see example 4).

In order to constitute this library, 6 000 clones selected on dishes of LB medium containing 50 mg/ml of ampicillin after transformation of electrocompetent cells of the *E. coli* strain DH5α are individually subcultured in wells of 96-cell [sic] microtitration plates containing 200 ml [sic] of Hogness culture and conservation medium (Sambrook et al. 1989) supplemented with 100 μg/ml of ampicillin. The stock plates thus constituted are incubated at 37° C. with moderate agitation of 160 rpm for 24 h such that the clones multiply and form saturated suspensions of bacteria having reached the stationary growth phase. The stock plates are then replicated in duplicate by individually re-seeding each well of two 96-cell [sic] plates containing 200 ml [sic] of LB culture medium supplemented with 100 μg/ml of ampicillin and 1 mM of IPTG using an aliquot of the cultures of each well of the stock plates. These plates thus obtained, called assay plates, are incubated for 24 h (37° C., 160 rpm) so that the clones multiply and form saturated suspensions of bacteria having reached the stationary growth phase. The presence of the plasmids pVRC706 in the bacterial cells is selected with ampicillin and expression of the papM methylase genes carried by these plasmids is induced by adding IPTG at the start of the culture. These plates are then frozen at −80° C. before the assaying of the methylation activities which is carried out on the crude bacterial suspensions (see example 1).

The stock plates, once replicated in duplicate, are conserved at −80° C. and constitute a long-term storage form of the 6 000 clones to be analyzed.

Example 4

Results of the Screening of the Library of *E. coli* Strain DH5α Harboring Plasmids pVRC706 on which Mutagenesis has been Performed This example illustrates the rapid analysis of a library of 6 000 clones using a miniaturized activity assay in order to select the clones harboring mutated genes encoding enzymes having advantageous properties.

4.1. Crude Results of the Screening of the 6 000 Clones

At the end of the first screening, performed as described in example 1, on the 6 000 clones of the library prepared in example 3, the following are selected:

441 clones exhibiting zero or undetectable methylation activity, i.e. a level of 7.3%;

9 clones exhibiting a first methylation reaction which is favored compared to the second reaction, i.e. clones having a ratio r (as defined in example 1.2) of greater than 0.6. The frequency of appearance of such mutants is therefore very low, it is 0.15%.

These first results are verified as described below.

4.2. Methodology for Confirmation of the Selected Clones

The methylation activities of all the clones selected during the first screening are systematically re-assayed using the replica plates prepared as in example 3, and by following the same protocol so as to confirm the results of the first assays. It appears that, for the great majority of the clones, the assay results are confirmed.

Thus, it is confirmed that:

360 clones exhibit zero methylation activity, i.e. a level of 6%.

8 clones exhibit a first methylation reaction which is favored compared to the second reaction, i.e. clones having a ratio r (as defined in example 1.2) of greater than 0.6. The frequency of appearance of such mutants is therefore very low, it is 0.13%.

For the 8 clones for which the ratio of the enzyme efficiency is such that r>0.60, two other confirmation steps are set up:

(1) The plasmid DNA of these clones is isolated using standard techniques (Sambrook et al., 1989) and re-introduced into fresh electrocompetent cells of the *E. coli* strain DH5α. This step makes it possible to verify that the alteration of the ratio r of the methylation activities, observed in the 8 clones, is not related to the chromosomal context of the clones, but depends only on the plasmids originating from the selected clones.

(2) The following verification step consists in recloning the papM genes present in the selected clones, into fresh expression vectors pMTL23. For this, the 1.7 kb MluI-BamHI fragments carrying the papM genes are isolated from the plasmid DNA extracted from the selected clones, and are recloned between the unique MluI and BamHI sites of pMTL23. The steps required for these clonings (isolation of plasmid DNA, digestion of plasmid DNA with restriction enzyme, migration and analysis of enzyme digestions by agarose gel electrophoresis, preparation of DNA fragments after electrophoretic migration, ligation reactions) were carried out according to the standard protocols described by Sambrook et al., (1989). The resulting plasmids have a structure similar to that of pVRC706 (FIG. 5) with the difference that they carry one of the 8 mutated alleles of the papM gene. They are called pVRC710 to pVRC717, each number being attributed to one of the 8 mutated alleles, and are reintroduced into fresh electrocompetent cells of the *E. coli* strain DH5α. The methylation activities of the resulting clones are re-assayed as described above. This step makes it possible to verify that the alteration of the ratio r of the methylation activities, observed in these clones, is not related to one (or more) mutation(s) which would be produced in a region of pVRC706 outside the papM gene, but depends only on one (or more) mutation(s) located in the papM gene.

All the verification steps make it possible to confirm the phenotype of 7 of the 8 mutants selected beforehand. For example, it is observed that the ratio of the two methylation activities, calculated as described in example 1.2, is 0.63 for the mutant 49 (clone 49C9) and 0.67 for the mutant 66 (clone 66A9), whereas it is only 0.40 for the clone expressing the wild-type papM gene in the same experiment.

Example 5

Genetic Characterization of the Mutant papM Genes Derived from the Mutagenesis Carried out with Hydroxylamine at 85° C. on the Plasmids pVRC706

This example illustrates the genetic characterization of the genes which have undergone the chemical mutagenesis. The genetic characterization is carried out by cloning and sequencing the mutated genes in order to compare their sequence to that of the wild-type gene and demonstrate the mutation(s) which account for the phenotypes observed. This genetic characterization is carried out in parallel to a biochemical characterization of the proteins encoded by the mutated genes (cf. example 7) in order to correlate the amino acid change(s) observed with the modifications of the catalytic properties noted for these enzymes.

5.1. Method

In the case of the papM genes derived from the mutagenesis carried out with hydroxylamine at 85° C. on the plasmids pVRC706, the papM genes of the 7 selected clones were subcloned and sequenced. The part of the 1.7 kb MluI-BamHI region of the plasmids pVRC706 on which mutagenesis was performed, carrying the mutated papM genes, was subcloned as two subinserts into vectors derived from the M13 phage (Messing et al., 1981) suitable for DNA sequencing by the Sanger method (Sambrook et al., 1989): the 0.7 kb SmaI-AgeI fragment containing the 3' portion of the papM gene was cloned at the SmaI site of the vector M13mp18 and the 0.4 kb SalI-PstI fragment containing the 5' portion was cloned between the SalI and PstI sites of the vectors M13mp18 and M13mp19 (FIG. 5). The steps required for these subclonings were carried out according to the standard protocols described by Sambrook et al., (1989). These two inserts were double-strand sequenced by the "Sanger" chain termination method using fluorescent dideoxynucleotides of the PRISM ready Reaction DyeDeoxy Terminator Cycle Sequencing Kit system marketed by Applied Biosystems. The sequencing reactions are carried out in a PCR machine on single-stranded DNA using, as synthesis primer, the universal primer (Sambrook et al., 1989) or oligonucleotides complementary to a 20-nucleotide sequence of the insert to be sequenced and synthesized by a Biosearch 8600 automated synthesizer (Blanc et al., 1995). The products of these reactions are then analyzed using an Applied Biosystems 370A automatic sequencer which performs electrophoretic migration of the sequences and reads them. The sequences are then processed using the programs of the BISANCE server of the Infobiogen bioinformatics center (Dessen et al., 1990) which enables, inter alia, concatenation thereof, translation thereof to protein, and comparison with the wild-type sequence.

5.2. Results

Initially, the following 7 clones were single-strand sequenced and the ratio r was redetermined (in an experiment for which the ratio for the wild-type PapM enzyme was found to be equal to 0.40)

| Mutant | Ratio | Mutation | Mutation (Nucl.) |
| --- | --- | --- | --- |
| 45 | 0.52 | Thr274 > Ile | ACC > ATC |
| 49 | 0.63 | Gly249 > Ser | GGC > AGC |
| 52 | 0.66 | Gly249 > Asp | GGC > GAC |
| 66 | 0.67 | Thr192 > Ile | ACC > ATC |
| 69 | 0.51 | Met226 > Ile | ATG > ATA |
| 74D4 | 0.63 | Gly249 > Ser | GGC > AGC |
| 74D5 | 0.52 | Met226 > Ile | ATG > ATA |

The results of the comparison of the sequences of the proteins encoded by the mutated papM genes derived from the mutagenesis carried out with hydroxylamine at 85° C. on the plasmids pVRC706, with the sequence of the protein encoded by the wild-type papM gene (Blanc et al., 1994; Blanc et al., 1997) are indicated in FIG. 7 and in the following table, for 2 of the 7 selected clones the sequence of which was verified on both strands.

TABLE 3

|  | Mutant 49 (clone 49C9) | Mutant 66 (clone 66A9) |
| --- | --- | --- |
| Nucleotide mutation in the papM gene | GGC > AGC | ACC > ATC |
| Amino acid substitution in the PapM protein | $Gly_{249}$ > Ser | $Thr_{192}$ > Ile |

In this table, only the mutations which cause an amino acid change in the corresponding protein are indicated. For some clones, and in particular for the clone 66A9, called mutant 66, other "silent" mutations were observed which do not lead to a change in the amino acid sequence due to the degeneracy of the genetic code.

It is noted that, for each of the 7 clones selected and sequenced, it is possible to demonstrate a point mutation in the papM gene leading to an amino acid change and corresponding effectively to the types of change C>T or G>A expected after treatment with hydroxylamine. Among the 7 clones analyzed, some of these mutations are found several times, such that these 7 clones can be divided up into 4 classes of mutants depending on the position affected. The clones described above represent 2 of the 4 classes thus constituted.

The effects of two mutations were more particularly studied in the remainder of this work; they are, with reference to the sequence SEQ ID No.1, firstly, the substitution of a cytosine at position 658 with a thymine (C658T) (mutated allele 66) and, secondly, the substitution of a guanine at position 828 with an adenine (G828A) (mutated allele 49).

In parallel with this genetic characterization, the biochemical characterization of the proteins encoded by the mutated genes as described in example 7 made it possible to observe a change in the catalytic properties of these enzymes compared to the protein encoded by the wild-type papM gene.

It is thus possible to correlate the amino acid changes observed with the modifications of the catalytic properties noted for these enzymes.

It is thus noted that, for the mutant 66, the amino acid modified is the threonine located at position 192 just before the NPPY motif located at positions 193 to 196 (FIG. 7). This motif is conserved in all the N-methylases and more particularly the DNA N-methylases (methylating the 6-positions of adenines and the 4-positions of cytosines) and is thought to be part of the catalytic domain of these enzymes (Schluckebier et al., 1995). Modification of the threonine residue, a polar amino acid, to an isoleucine residue which is hydrophobic, is therefore probably important for the catalytic properties of the corresponding protein. A considerable change in the catalytic properties of the enzyme encoded by the mutated gene 66, and more particularly for the second methylation reaction (cf. example 7) was in fact noted.

Example 6

Construction by Genetic Engineering of Doubly Mutated papM Genes using the Mutated papM Genes Derived from the Mutagenesis Carried out on the Plasmids pVRC706

This example illustrates the construction, by genetic engineering, of doubly mutated genes using genes exhibiting single mutations obtained after mutagenesis carried out with hydroxylamine on plasmid DNA (cf. example 2), selected by enzymatic screening (cf. example 4) and characterized by sequencing (cf. example 5). Surprisingly, the strategy made it possible to obtain more advantageous mutated genes accumulating the properties observed in the single mutants.

Several combinations of mutations taken in pairs were effected. By way of example, the combination of the mutations 49 and 66 is given in detail below. To this effect, a chimeric gene was produced by joining the 5' portion of the mutated papM gene 66 to the 3' portion of the mutated papM gene 49. To do this, the following DNA fragments are isolated:

the 0.65 kb MluI-XhoI fragment is isolated from the plasmid pVRC713 carrying the mutated papM gene 66 (cf. example 4). This fragment contains the beginning of the allele 66, including the ATC codon, which has been mutated and which encodes the isoleucine which is found at position 192 of the modified methylase 66 (see FIG. 7);

the 1.05 kb XhoI-BamHI fragment is isolated from the plasmid pVRC711 carrying the mutated papM gene 49 (see example 4). This fragment contains the end of the allele 49, including the AGC codon, which has been mutated and which encodes the serine which is found at position 249 of the modified methylase 49 (see FIG. 7).

These two fragments are co-cloned according to the standard protocols of Sambrook et al., (1989) between the unique MluI-BamHI sites of the plasmid pMTL23 (Chambers et al., 1988) so as to reconstitute a plasmid having a structure similar to that of pVRC706 (FIG. 5) with the difference that it carries the doubly mutated allele of the papM gene encoding a protein modified at positions 192 and 249. The resulting plasmid is called pVRC718 and allows expression of the doubly mutated gene 49/66 after transformation of electrocompetent cells of the E. coli strain DH5α and induction of the Plac promoter by adding 1 mM of IPTG.

The doubly mutated allele 49/66 is then transferred into a second expression vector pET11c (Novagen) using the strong PT7 promoter recognized by the T7 phage RNA polymerase. To do this, the 1.8 kb BglII-BamHI fragment carrying the papM gene 49/66 is isolated from the plasmid pVRC718 and is cloned at the unique BamHI site of pET11c. A recombinant plasmid, called pVRC721, described in FIG. 8, corresponding to the direction of insertion so as to produce translational fusion between gene 10 of the T7 phage and the papB gene located upstream of the papM gene, is selected. This plasmid is then introduced into the E. coli expression strain B121 (DE3) which allows expression of the T7 phage RNA polymerase and therefore of the papM gene 49/66 transcribed from the T7 promoter.

With a similar construct using the T7 phage expression system, an overproduction of the wild-type PapM protein 10 times greater than the production obtained with the plasmid pVRC706 has been observed (Blanc et al., 1997). The system using the T7 phage similarly makes it possible to overproduce the modified methylase encoded by the doubly mutated gene 49/66 with a view to purifying it and characterizing it as described in example 7.

Example 7

Biochemical Characterization of the Product of the papM Gene (Wild-Type or Mutated) of S. pristinaespiralis expressed in E. coli strains This example illustrates the determination of the kinetics constants for the reactions catalyzed by the PapM protein (mutated or wild-type). The PapM protein catalyzes two reactions; firstly methylation of 4-amino-L-phenylalanine (L-PAPA) to 4-methylamino-L-phenylalanine (L-MMPAPA) and, secondly, methylation of 4-methylamino-L-phenylalanine to 4-dimethylamino-L-phenylalanine (L-DMPAPA).

7.1. Assaying the Activity of Methylation of 4-amino-L-phenylalanine to 4-methylamino-L-phenylalanine and the Activity of Methylation of 4-methylamino-L-phenylalanine to 4-dimethylamino-L-phenylalanine This example illustrates the assaying of two terminal activities of the biosynthesis of 4-dimethylamino-L-phenylalanine, a component of pristinamycin Ia. These are, firstly, the methylation of 4-amino-L-phenylalanine to 4-methyl-amino-L-phenylalanine (methylation 1) and, secondly, the methylation of 4-methylamino-L-phenylalanine to 4-dimethylamino-L-phenylalanine (methylation 2), these two activities using SAM as methyl group donor (FIG. 4).

The enzyme fractions to be assayed (1 to 20 units) are incubated for 30 min at 27° C. in a total volume of 200 µl of 50 mM bis-tris-propane buffer, pH 6.8, containing SAM (200 µM) the methyl group of which is radioactively labeled with the carbon 14 isotope (2 Ci/mol), in the presence of 4-amino-L-phenylalanine (1 mM) for assaying methylation 1, or of 4-methylamino-L-alanine (2.5 mM) for assaying methylation 2.

The reaction is stopped by adding 16 µl of 37% hydrochloric acid and then 20 µl of sodium heptanesulfonate at 240 g/l. After centrifugation, 150 µl of supernatant are injected into the HPLC system in the following gradient mode:

Mobile phase: Eluent A=1.2 g of heptanesulfonate+2.5 ml of glacial acetic acid+water (qs 1 000 ml). Eluent B=1.2 g of sodium heptanesulfonate+2.5 ml of glacial acetic acid+300 ml of acetonitrile+water (qs 1 000 ml). The gradient is produced in the following way: at t=0, 30% of eluent B; t=16 (min), 30% of eluent B; t=17 (min), 100% of eluent B; t=20 min, 100% of eluent B; t=21 min, 30% of eluent B; t=25 (min), 30% of eluent B.

Stationary phase: Nucleosil® C 18 5 µm×4.6 mm column (Macherey-Nagel)

On leaving the column, the substrates and products of the enzyme reaction are quantified by absorption at 254 nm. This detection is coupled to an on-line radiochemical detection using a Berthold LB506 detector equipped with a solid scintillation cell of the GT400-U4 type. This makes it possible to specifically follow the incorporation of radioactive methyl groups into the reaction products.

The unit of enzyme activity for methylation 1 (and also for methylation 2) is defined as the amount of enzyme required to incorporate 1 nmol of methyl group into 4-amino-L-phenylalanine (or into 4-methylamino-L-phenylalanine).

7.2. Purification of the Recombinant Proteins of *S. pristinaespiralis* (Wild-type and Mutated) Exhibiting the SAM-dependent N-methyltransferase Activities Catalyzing the Methylation of 4-amino-L-phenylalanine to 4-methylamino-L-phenylalanine and the Methylation of 4-methylamino-L-phenylalanine to 4-dimethylamino-L-phenylalanine This example illustrates the purification of an enzyme of *S. pristinaespiralis* SP92, involved in the biosynthetic pathway for pristinamycin IA, expressed in *E. coli* by cloning of the modified papM gene.

7.2.a. Purification of the Mutant PapM Enzyme 49/66

Using the assay described previously in example 7.1, the SAM-dependent N-methyltransferase is purified as described below, taking care to freeze and conserve at −70° C. the active fractions between each step if necessary.

The centrifugation pellet from a culture of *E. coli* BL21 (DE3)::pVRC721 (cf. example 6) which overproduces the PapM variant 49/66 after induction with IPTG is washed with a 100 mM phosphate buffer, pH 7.2, containing 1 mM PMSF, 5 mM EDTA, 5 mM EGTA, 0.5 M KCl and 10% v/v of glycerol. Two grams of the washed pellet are taken up in 20 ml of 0.1 M Tris-HCl buffer, pH 8, containing 4 mM DTE, 5 mM benzamidine, 0.2 mM Pefabloc, 100 µg/l E-64, 2 mg/l leupeptin, 1 mM EDTA, 1 mM EGTA, 2 mg/l aprotinin, 20% glycerol and 2 mg/ml lysozyme. This buffer is kept at +4° C. The suspension thus obtained is vigorously agitated at +4° C. After 30 min of agitation, 0.2 mg/ml of deoxyribonuclease I and 5 mM MgCl$_2$ are added. After 90 min of agitation, the extract is centrifuged for 1 hour at 50 000 g. The supernatant is desalified, in 2.5 ml aliquots, by gel permeation on PD-10 columns (Pharmacia), equilibrated in a 20 mM bis-tris buffer, pH 6.8, containing 4 mM DTE, 5 mM benzamidine, 0.2 mM Pefabloc, 100 µg/l E-64, 2 mg/l leupeptin, 1 mM EDTA, 1 mM EGTA, 2 mg/l STI, 2 mg/l aprotinin and 20% v/v glycerol. A portion of the protein eluate is then chromatographed (34 mg of protein) on a MonoQ HR® 10/10 column at a flow rate of 3 ml/min with an increasing linear gradient of sodium chloride (0 to 0.3 M) in a 20 mM bis-tris buffer, pH 6.8, containing 4 mM DTE, 2 mM benzamidine, 100 µg/l E-64, 2 mg/l leupeptin and 20% v/v glycerol. On leaving the column, the fractions are made up with 10% v/v of 20 mM bis-tris buffer, pH 6.8, containing 4 mM DTE, 30 mM benzamidine, 2 mM Pefabloc, 100 µg/l E-64, 2 mg/l leupeptin, 5 mM EDTA, 5 mM EGTA, 10 mg/l STI, 10 mg/l aprotinin and 20% v/v glycerol. Under these conditions, the two methylation activities (1 and 2) are detected in an identical manner in the exclusion fractions and the first elution fractions. These fractions are pooled, concentrated by ultracentrifugation on Centriprep® 10 and then on Centricon® 10. This concentrate is brought to 0.85 M of ammonium sulfate and then chromatographed (20 to 80 mg in each cycle) on a Phenyl-Superose HR® 5/5 column at a flow rate of 0.5 ml/min with a decreasing linear gradient of ammonium sulfate (0.85 to 0 M) in a 50 mM bis-tris buffer, pH 6.8, containing 4 mM DTE, 2 mM benzamidine, 100 µg/l E-64, 2 mg/ml leupeptin, 1 mM EDTA, 1 mM EGTA and 10% v/v glycerol. On leaving the column, the fractions are made up with 10% v/v of 50 mM bis-tris buffer, pH 6.8, containing 4 mM DTE, 30 mM benzamidine, 2 mM Pefabloc, 100 µg/l E-64, 2 mg/l leupeptin, 1 mM EDTA, 1 mM EGTA, 10 mg/l STI, 10 mg/l aprotinin and 10% glycerol. Under these conditions, the two methylation activities (1 and 2) are detected in an identical manner in the elution fractions corresponding to approximately 0.15 M ammonium sulfate.

After this step, the enzyme is pure. It exhibits, by SDS-PAGE electrophoresis, a single band centered at a molecular weight in the region of 32 000.

TABLE 4

Purification of the mutant 49/66 4-amino-L-phenylalanine (phenyl N-)methyltransferase enzyme from the *E. coli* strain BL21(DE3)::pVRC721. The purification factor is calculated according to the increase in specific activity of the fractions during the purification.

| Purification step | Vol. (ml) | Proteins (mg) | Specific activity (units$^a$/mg) | Yield (%) | Purification factor |
|---|---|---|---|---|---|
| Crude extract | 4.3 | 33.7 | 3 400 | — | — |
| PD 10 | 6 | 31.5 | 3 400 | 93.5 | 1 |
| MonoQ HR 10/10 | 17.5 | 3.0 | 19 365 | 36.9 | 4.1 |
| Phenyl-Superose | 1 | 0.145 | 28 000 | 3.5 | 8.2 |

$^a$These are units of enzyme activity for methylation 1, defined in example 7.1.

7.2.b. Purification of the Wild-Type, Mutant 49 and Mutant 66 PapM Enzymes.

The PapM wt, papM 49 and papM 66 enzymes are purified from cultures of *E. coli* DH5α transformed respectively with the plasmids pVRC706, pVRC711 and pVRC713 (cf. example 4) and induced with IPTG. The purification protocol used is the same as that which is described in example 7.2.a.

7.3. Measurement of the Km and Vmax Kinetics Constants of the Purified PapM (Wild-Type and Mutated) Methylases The conditions for assaying the methylation activity are identical to those described in example 7-1, with the exception of the 2 mM concentration of SAM, the methyl group of which is radioactively labeled with the carbon 14 isotope (2 Ci/mol). Concentration ranges varying from 0.1 to 60 mM for each of the substrates 4-amino-L-phenylalanine for methylation 1 and 4-methylamino-L-phenylalanine for methylation 2 are prepared. For each concentration of each substrate, the reaction rate is measured and expressed in nmol converted per hour and per mg of proteins.

The values of the kinetics constants are deduced from the Michaelis-Menten curves plotted using the Enzfiter software.

The values obtained for the native wild-type PapM enzyme and for the mutant forms PapM 49, PapM 66 and PapM 49/66 are given in the table below.

TABLE 5

| Clone | PAPA | | MMPAPA | | Ratio Km2/Km1 | Ratio Vm1/Vm2 |
| | Km1 (mM) | Vm1 (nmol/h/mg) | Km2 (mM) | Vm2 (nmol/h/mg) | | |
|---|---|---|---|---|---|---|
| wt | 0.5 | 112 600 | 0.55 | 114 000 | 1.1 | 0.99 |
| 49 | 12 | 10 600 | 30 | 2 820 | 2.5 | 3.8 |
| 66 | 0.57 | 45 200 | 2.2 | 19 700 | 3.9 | 2.3 |
| 49/66 | 9 | 28 000 | 22 | 9 100 | 2.5 | 3.1 |

These results show that it is possible to obtain, using this method, a novel enzyme showing novel catalytic properties compared to the natural enzyme. For each mutant form of the enzyme, the enzyme efficiency of each methylation reaction (methylation 1 and methylation 2) was determined. This efficiency is defined by the ratio Vm1/Km1 (methylation 1) or Vm2/Km2 (methylation 2).

Then, for each form, the ratio of the enzyme efficiencies (methylation reaction 1/methylation reaction 2) was determined. This ratio is equal to Vm1.Km2/Vm2.Km1.

The ratio obtained for the wild-type PapM enzyme is 1.1.

The PapM mutants were selected such that the ratio of the enzyme efficiencies is greater than 2.5. The best mutants showed ratios of greater than 7, and preferably in the region of 10.

TABLE 7

| | Km1 | Vm1 | Km2 | Vm2 | Vm1/Km1 | Vm2/Km2 | Vm1·Km2 / Vm2·Km1 |
|---|---|---|---|---|---|---|---|
| wt | 0.5 | 112 600 | 0.55 | 114 000 | 225 200 | 207 270 | 1.08 |
| 49 | 12 | 10 600 | 30 | 2 820 | 880 | 94 | 9.36 |
| 66 | 0.57 | 45 200 | 2.2 | 19 700 | 79 300 | 8 950 | 8.86 |
| 49/66 | 9 | 28 000 | 22 | 9 100 | 3 110 | 410 | 7.58 |

7.4 Competition Assay Between the Two Substrates 4-amino-L-phenylalanine and 4-methylamino-L-phenylalanine This example illustrates how we were able to discriminate the most efficient methylase for producing PIB, i.e. the one which best catalyzes the first reaction of methylation of p-amino-L-phenylalanine to p-methyl-L-phenylalanine compared to the second reaction of methylation of p-methyl-L-aminophenyl-alanine to p-dimethylamino-L-phenylalanine.

The ratio of the rates of conversion of the two competitive substrates is given by the formula:

$$V1/V2 = (Kcat1/Km1)[S1] / (Kcat2/Km2)[S2]$$

Kcat being the "turnover" of the enzyme or the number of moles of methylated substrate per number of moles of enzyme and per unit of time.

This formula is valid for all concentrations of S1 and of S2.

In fact, whatever the concentrations of S1 and of S2 present, the enzyme reaction is the sum of two components, as if it was catalyzed by two separate enzymes, one acting on S1 and inhibited competitively by S2, the other acting on S2 and inhibited competitively by S1.

Any modification of the Km and/or of the Vmax of one of the two substrates would have consequences on the rate of conversion of the other and would lead to a variation in the ratio V1/V2.

The amount of substrate and of enzyme brought into play is thus avoided by taking care not to convert not more than 2% of each of the substrates.

Using the same conditions for assaying the methylation activity as those described in example 7-1, with the exception of the concentration of SAM, which is 2 mM, and the methyl group of which is radioactively labeled with the carbon 14 isotope (2.5 Ci/mol), and with the simultaneous presence of the two substrates at the concentrations, for 4-amino-L-phenylalanine, of 1 mM and, for 4-methylamino-L-phenylalanine, of 2 mM, the rate of each of the reactions could thus be determined.

The assays were carried out simultaneously on the mutants described in examples 4 to 6, using the same substrate solutions.

Under these conditions, the doubly mutated methylase 49/66 appears to be the most selective; it catalyzes the first methylation reaction 7 times better than the second, whereas the native enzyme catalyzes the two reactions in a similar manner.

Example 8

Construction of Recombinant Strains of *S. pristinaespiralis* Disrupted in the papM Gene This example illustrates the construction of recombinant strains of *S. pristinaespiralis* disrupted in the papM gene. Such strains constitute the first step in constructing recombinant strains in which the wild-type papM gene is replaced with one of the mutated alleles obtained and characterized as described in the preceding examples. In addition, these strains produce mainly a compound of the PI family, PINH2 (FIG. 3), which is not naturally synthesized by the strains having the wild-type papM gene. These strains therefore represent a pathway for obtaining PINH2 which it would be impossible to isolate from strains not disrupted in the papM gene.

8.1. Construction of Recombinant Strains Disrupted in the papM Gene

The disruption of the papM gene was carried out in several strains of *S. pristinaespiralis:* the strain *S. pristinaespiralis* SP92 previously described, which produces a mixture of PI and PII (Blanc et al., 1994);

the strain SP213 derived from SP92 after chemical mutagenesis. This strain produces specifically PIs.

The strategy for constructing recombinant strains disrupted in the papM gene is the same as for these two strains. The results obtained with the strain SP213 are given in detail in the remainder of this example.

This construct was prepared using the plasmid pVRC1303 (cf. FIG. 9) derived from the suicide vector pDH5 capable of replicating only in *E. coli* and carrying a resistance gene which is expressed in *Streptomyces* (Hillemann et al., 1991).

8.1.1. Construction of the Plasmid pVRC1303

The plasmid pVRC1303 was constructed after 4 main cloning steps described in FIG. 9, using:

the vector pDH5 carrying an origin of replication which is functional in *E. coli*, the ampicillin resistance gene which is expressed in *E. coli* and the gene for resistance to thiostrepton and to nosiheptide which is expressed in *Streptomyces* (Hillemann et al., 1991);

the plasmid pVRC409 (Blanc et al., 1994) for preparing the 2.5 kb BsiWI-PstI fragment carrying part of the pristinamycin cluster genes located downstream of the papM gene;

the plasmid pVRC900 (Blanc et al., 1994; Blanc et al., 1997) for preparing the 3.3 kb PvuII-PvuII fragment carrying part of the pristinamycin cluster genes located upstream of the papM gene;

the plasmids pHP45Ω-Km (Fellay et al., 1987) and pU702 (Hopwood et al., 1985) for preparing, after an intermediate cloning step, the 3.7 kb EcoRI-EcoRI fragment carrying essentially the kanamycin resistance gene which is expressed in *E. coli* and in *Streptomyces*. This Ω-Km cassette carrying the kanamycin resistance gene is introduced between the regions upstream and downstream of the papM gene, cloned into pVRC1303, and replaces the missing papM gene (FIG. 9).

All the steps required for these clonings (plasmid DNA isolation, plasmid DNA digestion with restriction enzyme, filling of overhanging 5' ends by treatment with Klenow enzyme, migration and analysis of enzyme digestions by agarose gel electrophoresis, preparation of DNA fragments after electrophoretic migration, ligation reactions, transformation of *E. coli*, selection and analysis of the recombinant clones) were carried out according to the standard protocols described by Sambrook et al. (1989).

8.1.2. Construction of Recombinant Strains of *S. pristinaespiralis* Disrupted in the papM Gene by Homologous Recombination with the Plasmid pVRC1303

The recombinant strains were isolated after transformation of the strain SP213 with the plasmid pVRC1303.

Preparation of the protoplasts of these strains and transformation thereof by the method using PEG were carried out as described in Hopwood et al. (1985). After transformation with 5 times 1 µg of pVRC1303, the protoplasts are plated out on R2YE medium (Hopwood et al., 1985) and selected, after regeneration overnight, by overlaying 3 ml of SNA medium containing 10 µg/ml of kanamycin.

Out of the 5 transformations carried out, 37 kanamycin-resistant clones were isolated. These recombinants can result:
  either from an integration into the chromosome of the plasmid pVRC1303 subsequent to a simple homologous recombination event between the chromosomal and plasmid regions located upstream or downstream of the papM region (in the case of simple crossing over);
  or from an exchange between the plasmid Ω-Km cassette carrying the kanamycin resistance gene and the chromosomal papM gene, subsequent to a double homologous recombination event between the chromosomal and plasmid regions located upstream or downstream of the papM gene (in the case of double crossing over represented in FIG. 10).

In these two cases, the Ω-Km cassette is transferred onto the chromosome of the recombinant strain and confers on it resistance to kanamycin. On the other hand, it is only in the case of simple crossing over that the gene present in the plasmid pVRC1303 (FIG. 9) is transferred onto the chromosome of the recombinant strain and confers on it resistance to thiostrepton and/or to nosiheptide (Hillemann et al., 1991). The two crossing over situations (simple or double crossing over) can therefore be distinguished by analyzing the phenotype of resistance or sensitivity to nosiheptide.

To do this, the recombinant clones derived from the 5 transformations with pVRC1303 and selected for their resistance to 10 µg/ml of kanamycin, as described above, were subcultured in the form of patches on HT medium (Hopwood et al., 1985) containing 10 µg/ml of kanamycin, and then tested on HT medium containing 400 µg/ml of nosiheptide. Only the clones exhibiting the phenotype (Kana$^R$,Nosi$^S$) were selected since they correspond to the double crossing over case sought. These recombinant clones were then purified in the following way: a stock of spores of these clones is prepared according to the method of Hopwood et al. (1985), after plating out and growth on HT medium containing 10 µg/ml of kanamycin, which is then diluted and re-plated out on the same medium in order to obtain isolated colonies. These colonies constitute pure subclones of the selected clones. Two subclones derived from 5 different clones were thus analyzed.

In order to verify the chromosomal structure of these subclones, their genomic DNA is extracted after having cultured them in liquid YEME medium containing 10 µg/ml of kanamycin, according to the technique of lysis with lysozyme and extraction with phenol/chloroform described by Hopwood et al. (1985). Several rounds of Southern blotting of the total DNA of these various clones, digested with EcoRI and SphI, are performed, hybridizing with the plasmid pVRC1303 linearized with EcoRI and used as a probe after labeling by random priming obtained with ($\alpha$-$^{32}$P)dCTP and the labeling kit (random primed DNA labeling kit) marketed by Amersham. The techniques used are those described in Sambrook et al. (1989). The hybridization results clearly show that the subclones were obtained by double crossing over between the vector pVRC1303 and the chromosome of the strain SP213 described in FIG. 10. The presence in these subclones of a 9.9 kb EcoRI fragment which hybridizes with the probe, which is not present in the wild-type strain SP213 for which the size of the EcoRI fragment which hybridizes is 6.8 kb, is verified in particular.

One of the clones having the genotype SP213ΔpapM::Ω kanar was called SP216. This clone was selected for analysis of its production and for continuing with the genetic constructs with a view to obtaining recombinant strains in which the wild-type papM gene was replaced with one of the mutated or doubly mutated alleles of papM as described in the preceding examples.

8.2. Production of Pristinamycins by the Mutant SP216

This example illustrates how it is determined that the mutant of *S. pristinaespiralis* SP216 disrupted in the papM gene produces mainly PINH2 [4ζ-amino-de(4ζ-dimethylamino)pristinamycin IA] under standard fermentation conditions. The structure of PINH2 is represented in FIG. 2.

The mutant SP216 and also the control wild-type strain SP213 were cultured in liquid production medium. The fermentation was carried out as follows: 0.5 ml of a suspension of spores of the abovementioned strain are added, under sterile conditions, to 40 ml of inoculum medium in a 300 ml baffled Erlenmeyer flask. The inoculum medium consists of 10 g/l of Corn Steep, 15 g/l of sucrose, 10 g/l of $(NH_4)_2SO_4$, 1 g/l of $K_2HPO_4$, 3 g/l of NaCl, 0.2 g/l of $MgSO_4.7H_2O$ and 1.25 g/l of $CaCO_3$. The pH is adjusted to 6.9 with sodium hydroxide before introducing the calcium carbonate. The Erlenmeyer flasks are shaken for 44 h at 27° C. on a rotary shaker at a rate of 325 rpm. 2.5 ml of the preceding 44 h culture are added sterilely to 30 ml of production medium in a 300 ml Erlenmeyer flask. The production medium consists of 25 g/l of soybean flour, 7.5 g/l of starch, 22.5 g/l of glucose, 3.5 g/l of forage yeast, 0.5 g/l of zinc sulfate and 6 g/l of calcium carbonate. The pH is adjusted to 6.0 with hydrochloric acid before introducing the calcium carbonate.

The Erlenmeyer flasks are shaken for 50 h at 27° C. As soon as the fermentation is over, the volume of must is measured and two volumes of mobile phase composed of 34% of acetonitrile and 66% of a 0.1 M $KH_2PO_4$ solution (adjusted to pH 2.9 with concentrated $H_3PO_4$) are added, allowing extraction of the pristinamycins. After shaking, the entire mixture is filtered; the pristinamycins are contained in the supernatant. They are then assayed by HPLC, injecting 150 μl of the centrifugation supernatant onto a Nucleosil 5-C8® column of 4.6×150 mm, eluted with a mixture of 40% acetonitrile and 60% 0.1 M phosphate buffer, pH 2.9. The pristinamycins are detected by UV absorption at 206 nm and, optionally, by their fluorescence emission (370 nm filter, excitation at 306 nm). The production of pristinamycins is given in the tables below.

TABLE 8

Level of PINH2 production (in mg/l) of the strains SP213 and SP216

| Strain | PINH2 |
|---|---|
| SP213 (papM wt) | <0.1 |
| SP216 (ΔpapM :: Ω kanaR) | 7 |

These results show that, under the fermentation conditions produced, the mutant SP216 produces essentially PINH2, whereas the control SP213 produces a standard amount of PI, which includes mainly PIA.

Example 9

Construction of Recombinant Strains of *S. pristinaespiralis* Comprising the Allele 49/66 papM Gene or the Allele 66 papM Gene This example illustrates the ability of the recombinant strains of *S. pristinaespiralis* mutated in the papM gene to selectively produce a compound of the PI family, PIB (FIG. 2). PIB is synthesized naturally by strains having the wild-type papM gene, but at very low levels of a maximum of approximately 5%. These strains therefore represent a pathway for obtaining PIB thus produced in large amount and very specifically.

9.1 Construction of Recombinant Strains Mutated in the papM Gene

The mutated papM gene 49/66 was introduced into the strain *S. pristinaespiralis* SP92 previously described which produces a mixture of PI and PII (Blanc et al., 1994), and into the strain SP213 derived from SP92 after chemical mutagenesis; the strain SP213 produces specifically PIs.

The mutated papM gene 66 was introduced into the strain SP213 derived from SP92.

The strategy for constructing recombinant strains carrying one of the mutated alleles of the papM gene is the same whatever the type of mutation of the papM gene allele (49/66 or 66) and whatever the strain chosen. It consists in transforming the recombinant strains in which the wild-type papM gene has been disrupted and replaced with an Ω-Km cassette (cf. example 8), with a suicide plasmid which allows exchange of this cassette with one of the mutated alleles of papM.

By way of illustration, details are given below of the introduction of the allele 49/66 mutated papM gene into the strain SP216 (production of the strain SP216 is described in example 8). This construction was carried out using the plasmid pVRC1306 (cf. FIG. 11) derived from the suicide vector pDH5 capable of replicating only in *E. coli* and carrying a gene for resistance to thiostrepton or to nosiheptide which is expressed in *Streptomyces* (Hillemann et al., 1991).

Example 9.2 gives the results of production of pristinamycins obtained with several recombinant strains derived from SP92 or from SP213 and expressing either the mutated papM gene 66 or the mutated papM gene 49/66.

9.1.1. Construction of the Plasmid PVRC1306

The plasmid pVRC1306 comprising [sic] carrying the allele 49/66 papM gene was constructed from the plasmid pVRC1303 carrying a deletion of the papM gene. This construction is carried out in three steps as described in FIG. 11. For these clonings, the following plasmids were used:

the plasmid pBR322 is a vector for cloning in *E. coli*, which was used as an intermediate vector for transferring the 8.9 kb EcoRI fragment of pVRC1303 described in example 8.1.1 and containing, inter alia, the papM gene deleted with the Ω-Km cassette carrying the kanamycin resistance gene. The cloning was carried out at the EcoRI site of pBR322 and the plasmid obtained was called pVRC1304.

the plasmid pVRC 721 described in example 6 (FIG. 6) was used to prepare the 1 kb MluI/AgeI insert containing the allele 49/66 papM gene. This insert was then exchanged with the 4 kb MluI/AgeI fragment of pVRC1304 and the plasmid obtained was called pVRC1305.

the plasmid pVRC1303 made it possible to exchange the 8.9 kb EcoRI fragment with the 5.83 kb EcoRI fragment of pVRC1305 containing the allele 49/66 papM gene.

The final plasmid, pVRC1306 (FIG. 11), therefore comprises the allele 49/66 papM gene and also a portion upstream and downstream of this gene, the entire assembly being cloned into the vector pDH5 described in example 8.1.1.

9.1.2. Construction of Recombinant Strains of *S. pristinaespiralis* mutated in the allele 49/66 papM gene by homologous recombination with the plasmid pVRC1306

The recombinant strains were isolated after transformation of the strain SP216 described in example 8 with the plasmid pVRC1306. For this, two steps were necessary. The first step consisted in selecting, by analysis of the phenotype ($Kana^R$, $Nosi^R$), a strain derived from a simple homologous recombination event between the chromosomal and plasmid regions located upstream of the papM gene (FIG. 12). The second step consisted in selecting, using the strain ($Kana^R$, $Nosi^R$), the second homologous recombination event by analysis of the phenotype ($Kana^S$, $Nosi^S$) of the clones obtained (FIG. 13).

The carrying out of these two steps is described below.

The preparation of the protoplasts of these strains and the transformation thereof by the method using PEG were carried out as described in Hopwood et al. (1985). Ten independent transformations were carried out with, for each one, 1 μg of pVRC1306. The protoplasts were plated out on R2YE medium (Hopwood et al., 1985) and selected, after overnight regeneration, by overlaying 3 ml of SNA medium containing 400 μg/ml of nosiheptide.

Out of the 10 transformations carried out, 7 clones resistant to nosiheptide (Hillemann et al., 1991) were isolated. These recombinants result from an integration into the chromosome of the plasmid pVRC1306 subsequent to a simple homologous recombination event between the chromosomal and plasmid regions located upstream of the papM gene, which confers on these clones a double resistance, both to kanamycin (due to the transformed strain) and to thiostrepton (due to the recombination of the plasmid). The 7 recombinant clones were therefore subcultured on HT medium with 10 μg/ml of kanamycin and on HT medium with 400 μg/ml of nosiheptide. All of the clones exhibit the expected phenotype (Kana$^R$, Nosi$^R$). These clones were purified twice according to the following method: a stock of spores of these clones is prepared according to the method of Hopwood et al. (1985) and isolated colonies are obtained after plating out various dilutions of the stock on HT medium containing 400 µg/ml of nosiheptide. These colonies constitute pure subclones of the selected clones. The chromosomal structure of two subclones derived from two clones was analyzed by Southern blotting.

The genomic DNA was extracted after culturing in YEME liquid medium containing 4 µg/ml of nosiheptide. The DNA was extracted by treatment with lysozyme and extraction with phenol/chloroform according to the technique described by Hopwood et al. (1985). Several rounds of Southern blotting were carried out with the total DNA of these various subclones digested with the EcoRI and AseI restriction enzymes. The 8.9 kb fragment derived from pVRC1303 digested with EcoRI was used as a probe after labeling by random priming obtained with (α-32P) dCTP and the labeling kit (random primed DNA labeling kit) marketed by Amersham. The techniques used are those described by Sambrook et al. (1989). The hybridization results (bands corresponding to 6.83, 3.42, 3.125 and 2.06 kb) clearly showed that the subclones were obtained by simple crossing over between the vector pVRC1306 and the chromosome of the strain SP216. The DNA of the strain SP216 exhibits the bands corresponding to 4.42, 3.125 and 2.06 kb, but does not exhibit the band corresponding to that of 6.83 kb.

One of these clones was called SP216::pVRC1306.

The second step consists in selecting a second homologous recombination event between the chromosomal and plasmid regions located downstream of the papM gene, using the strain SP216::pVRC1306 (cf. FIG. 13). This step leads to the selection of recombinant clones which have exchanged the papM gene deleted with the Ω-Km cassette, with the allele 49/66 papM gene; the expected phenotype of the recombinant clones is (Kana$^S$,Nosi$^S$).

Using the clone SP216::pVRC1306, 2 growth cycles were performed at 30° C. on a rotary shaker at a rate of 325 rpm in order to promote the second recombination event. The first cycle was carried out with 200 µl of a stock of SP216::pVRC1306 spores in 10 ml of YEME medium (culture conditions: 30° C., 280 rpm, 72 hours), the second cycle was carried out with 800 µl of the suspension of the first cycle in 40 ml of YEME medium (culture conditions: 30° C., 280 rpm, 72 hours). The second culture was centrifuged for 15 min at 3 500 rpm, the pellet was taken up in 600 µl of water +0.01% Tween, and this suspension was plated out on HT medium in order to obtain layers of spores. In order to purify the recombinant clones derived from this liquid culture, the spores were harvested and dilute suspensions of these spores were plated out on HT medium in order to obtain isolated colonies.

To select clones having the desired phenotype (Kana$^S$, Nosi$^S$), 1 000 isolated colonies were subcultured and screened. These colonies were automatically subcultured on HT medium without antibiotic and on HT medium with 10 µg/ml of kanamycin. This first step made it possible to select 18 recombinant Kana$^S$ clones. From the HT medium without antibiotic, these 18 clones were manually picked and subcultured on HT medium without antibiotic, on HT medium with 10 µg/ml of kanamycin and on HT medium with 400 µg/ml of nosiheptide. Three recombinant clones having the phenotype (Kana$^S$,Nosi$^S$) were selected as being potentially derived from a double crossing over event. These clones were purified, a stock of spores was prepared from a spore layer and a genomic analysis was performed, the methods used being described above.

The chromosomal analysis of the recombinant subclones is carried out in two steps: the first step consists in verifying that the allele 49/66 papM gene is present and that the chromosomal regions upstream and downstream of this gene have not been modified. The second step consists in verifying the absence of DNA fragment corresponding to the W-Km cassette and to the plasmid pDH5.

For the first step, preparations of genomic DNA of the recombinant clones were produced and analyses of total DNA were carried out by Southern blotting according to the methods mentioned above. The total DNA was digested with the EcoRI and AseI restriction enzymes. The plasmid pVRC721 was digested with MluI (1.7 kb insert containing the allele 49/66 papM gene). This labeled fragment was used as a probe which hybridizes with a fragment corresponding to a band of 6.83 kb.

In addition, the total DNA was digested with SalI. Labeled fragments derived from pVRC409 and from pVRC803 (containing the regions upstream and downstream of the papM gene of the strain SP213, Blanc et al., 1994; Blanc et al., 1997) were used as probes. These fragments made it possible to reveal, after hybridization, 7 bands (2.45, 0.190, 2.150, 0.725, 1.55, 0.4 and 0.55 kb).

The second step consisted in verifying that there was no more DNA fragment corresponding to the Ω-Km cassette or to the plasmid pDH5. The total DNA was digested with EcoRI and AseI. The 2.2 kb HindIII fragment (Ω-Km cassette) of pHP45 Ω-Km (Fellay et al., 1987) and also pDH5 were used as probes.

The three recombinant clones exhibit a chromosomal profile (FIG. 13) which confirms the presence of the allele 49/66 papM gene and the absence of the kanamycin resistance gene and also of the fragment corresponding to the plasmid pDH5. These elements indicate that the genomic environment of the allele 49/66 papM gene is intact. A clone was selected and was called strain SP217.

In the same way, other strains of *S. pristinaespiralis* integrating the allele 49/66 mutated papM gene or the allele 66 papM gene were constructed. They are the strains:

SP101 derived from transformation of the strain SP 92 with the plasmid pVRC1306 carrying the allele 49/66 mutated papM gene;

SP218 derived from transformation of the strain SP216 with a plasmid equivalent to pVRC1306 but in which the allele 49/66 mutated papM gene has been replaced with the allele 66 mutated papM gene.

9.2. Production of Pristinamycins by the *P. pristinaespiralis* strains SP213, SP217, SP218, SP100 and SP101

This example shows the production of pristinamycins with the various mutants. It illustrates in particular the increase in production of PIB of the allele 49/66 mutated papM mutants (strain SP217) and of the allele 66 papM mutants (strain SP218) compared to the control papM wt strain (strain SP213). The effect of the allele 49/66 mutated papM gene (strain SP101) was also compared with respect to the control papM wt strain (strain SP92).

The techniques for producing, extracting and assaying the pristinamycins are identical to those described in example 8.2.

The levels of production of various pristinamycins expressed relative to the amount of PIA of the control strains (SP213 and SP92) are given in the table below.

TABLE 9

Production of pristinamycins PI for various *S. pristinaespiralis* strains. The values of PI produced are given in mg/liter.

| Strain | PIA | PIB | PINH2 | Other PIs |
|---|---|---|---|---|
| SP213 (papM wt) | 474 | 39 | 0 | 25 |
| SP217 (papM 49/66) | 0 | 162 | 57 | 19 |
| SP218 (papM 66) | 19 | 271 | 14 | 32 |

TABLE 9-continued

Production of pristinamycins PI for various *S. pristinaespiralis* strains. The values of PI produced are given in mg/liter.

| Layer | PIA | PIB |
|---|---|---|
| SP92 (papM wt) | 100 | 3 |
| SP101 (papM 66) | 0 | 11 |

These results confirm that the genes expressing the papM polypeptide variants according to the invention confer on the strains of *S. pristinaespiralis* an excellent selectivity for the production of PIB.

The invention claimed is:

1. A nucleic acid encoding a variant of the PapM polypeptide of bacteria of the *Streptomyces* genus comprising SEQ ID NO:2, selected from the group consisting of
 a polypeptide comprising the sequence of wild-type PapM polypeptide of *S. pristinaespiralis* modified by the replacement of residue Gly 249,
 a polypeptide comprising the sequence of wild-type PapM polypeptide of *S. pristinaespiralis* modified by the replacement of residue Thr 192,
 a polypeptide comprising the sequence of wild-type PapM polypeptide of *S. pristinaespiralis* modified by the replacement of residues Gly 249 and Thr 192, and
wherein the variant of the PapM polypeptide
 catalyzes at least one of the methylation of PAPA to MMPAPA and the methylation of MMPAPA to DMPAPA and
 exhibits an efficiency of methylation, as defined by the ratio Kcat/Km, which differs from the efficiency of methylation of the wild-type PapM polypeptide of *S. pristinaespiralis* for at least one of the methylations of PAPA or MMPAPA.

2. A nucleic acid comprising SEQ ID NO. 1 modified by mutation for the replacement of at least one of Gly 249 or Thr 192 and optionally modified by the replacement of at least one codon with an alternate codon encoding the same amino acid due to the degeneracy of the genetic code.

3. The nucleic acid as claimed in claim 2, which comprises at least one missense mutation upstream of the NPPY motif located at positions 193 to 196 of SEQ ID NO: 2.

4. The nucleic acid as claimed in claim 3, wherein the missense mutation leads to a non-conservative amino acid change.

5. The nucleic acid as claimed in claim 4, which comprises the substitution of a cytosine at position 658 with a thymine (C658T) of SEQ ID NO: 1.

6. The nucleic acid as claimed in claim 2, which comprises the substitution of a guanine at position 828 with an adenine (G828A) of SEQ ID NO: 1.

7. The nucleic acid as claimed in claim 4, which comprises the substitution of a guanine at position 828 with an adenine (G828A), and the substitution of a cytosine at position 658 with a thymine (C658T) of SEQ ID NO: 1.

8. An expression vector which replicates autonomously or which integrates in a bacterial strain, comprising the nucleic acid as claimed in claim 1.

9. A host cell containing a nucleic acid as claimed in claim 1 or claim 2.

10. The host cell as claimed in claim 9, selected from the group consisting of *E. coli*, *S. pristinaespiralis*, *Streptomyces olivaceus* ATCC12019, *Streptomyces ostreogriseus* ATCC27455, *Streptomyces mitakaensis* ATCC15297, *Streptomyces loïdensis* ATCC11415, *Streptomyces graminofaciens* and *Streptomyces diastaticus*.

* * * * *

UNITED STATES PATENT AND TRADEMARK OFFICE
CERTIFICATE OF CORRECTION

| | | |
|---|---|---|
| PATENT NO. | : 7,604,970 B2 | Page 1 of 1 |
| APPLICATION NO. | : 10/603282 | |
| DATED | : October 20, 2009 | |
| INVENTOR(S) | : Nathalie Bamas-Jacques et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 1,532 days.

should read (*) Notice: Subject to any disclaimer, the term of this patent is extended or adjusted under 35 U.S.C. 154(b) by 1,882 days.

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,604,970 B2
APPLICATION NO. : 10/603282
DATED : October 20, 2009
INVENTOR(S) : Nathalie Bamas-Jacques et al.

It is certified that error appears in the above-identified patent and that said Letters Patent is hereby corrected as shown below:

In column 4, line 45-46, delete "SEQ D No. 1." and insert -- SEQ ID No. 1. --, therefor.

In column 9, line 40, delete "$V1/V2=(Vmax1//Km1)$ [S1]/$(Vmax2/Km2)$ [S2]" and insert -- $V1/V2=(Vmax1/Km1)$ [S1]/$(Vmax2/Km2)$ [S2] --, therefor.

In column 19, line 66-67, delete "the-extract" and insert -- the extract --, therefor.

In column 23, line 43, delete "kananycin." and insert -- kanamycin. --, therefor.

In column 24, line 38, delete "Kanar" and insert -- kanaR --, therefor.

In column 26, line 7, delete "PVRC1306" and insert -- pVRC1306 --, therefor.

In column 33, line 47-51, in claim 2, delete "A nucleic acid comprising SEQ ID NO. 1 modified by mutation for the replacement of at least one of Gly 249 or Thr 192 and optionally modified by the replacement of at least one codon with an alternate codon encoding the same amino acid due to the degeneracy of the genetic code." and insert -- The nucleic acid of claim 1, wherein the polypeptide is modified by mutation of Gly 249 or Thr 192 of SEQ ID NO: 2 with another amino acid; and optionally modified by the replacement of at least one codon in the encoding nucleic acid sequence of SEQ ID NO: 1 with an alternate codon encoding the same modified amino acid at position 249 or 192 due to degeneracy of genetic code. --

Signed and Sealed this

Fifth Day of October, 2010

David J. Kappos
*Director of the United States Patent and Trademark Office*